US012778796B2

(12) United States Patent
Stich et al.

(10) Patent No.: US 12,778,796 B2
(45) Date of Patent: Nov. 3, 2026

(54) ADDED OR ALTERNATE THERMAL CONTACT PAD ADHESION

(71) Applicant: C. R. Bard, Inc., Franklin Lakes, NJ (US)

(72) Inventors: Madeline Stich, Thornton, CO (US); Gabriel A. Johnston, Broomfield, CO (US); Sean E. Walker, Platteville, CO (US); Rebecca D. Salisbury, Lafayette, CO (US); Michael R. Hoglund, Windsor, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 641 days.

(21) Appl. No.: 18/085,566

(22) Filed: Dec. 20, 2022

(65) Prior Publication Data

US 2023/0190519 A1 Jun. 22, 2023

Related U.S. Application Data

(60) Provisional application No. 63/292,319, filed on Dec. 21, 2021.

(51) Int. Cl.
*A61F 7/02* (2006.01)

(52) U.S. Cl.
CPC ........ *A61F 7/02* (2013.01); *A61F 2007/0212* (2013.01); *A61F 2007/0219* (2013.01);
(Continued)

(58) Field of Classification Search
CPC ...... A61F 2007/0054; A61F 2007/0212; A61F 2007/0219; A61F 2007/0228;
(Continued)

(56) References Cited

U.S. PATENT DOCUMENTS 2,167,865 A 8/1939 Beecher
2,250,325 A 7/1941 Barnes
(Continued)

FOREIGN PATENT DOCUMENTS

AU 678753 B3 6/1997
AU 2007201161 B2 12/2010
(Continued)

OTHER PUBLICATIONS

PCT/US2021/065144 filed Dec. 23, 2021 International Search Report dated Oct. 4, 2022.
(Continued)

*Primary Examiner* — Tigist S Demie
(74) *Attorney, Agent, or Firm* — Rutan & Tucker LLP

(57) ABSTRACT

A medical pad for exchanging thermal energy between a targeted temperature management (TTM) fluid and a patient. The medical pad includes a fluid containing layer configured for circulation of a TTM fluid therein. The pad may further include a bistable stiffening structure configured to transition between a first stable shape and a second stable shape. The pad may further include a thermally-conductive compressible foam layer disposed between the fluid containing layer and a patient contact side of the pad. a self-adhering stretchable band configured to secure the pad to the patient. The pad may further include a semi-permeable layer disposed between an underside of the fluid containing layer and a hydrogel layer so that the TTM fluid may migrate from the fluid containing layer to the hydrogel layer.

23 Claims, 5 Drawing Sheets

(52) U.S. Cl.
CPC ................ *A61F 2007/0228* (2013.01); *A61F 2007/0246* (2013.01); *A61F 2007/0258* (2013.01)

(58) Field of Classification Search
CPC ...... A61F 2007/0231; A61F 2007/0246; A61F 2007/0258; A61F 2007/026; A61F 7/02
See application file for complete search history.

(56) References Cited

U.S. PATENT DOCUMENTS

| | | | |
|---|---|---|---|
| 2,296,207 | A | 9/1942 | Joyce |
| 2,595,328 | A | 5/1952 | Bowen |
| 2,602,302 | A | 7/1952 | Poux |
| 2,726,658 | A | 12/1955 | Chessey |
| 2,807,809 | A | 10/1957 | Kottemann |
| 3,075,529 | A | 1/1963 | Young, Jr. |
| 3,091,242 | A | 5/1963 | Johnson et al. |
| 3,212,286 | A | 10/1965 | Curtis |
| 3,506,013 | A | 4/1970 | Zdenek |
| 3,734,293 | A | 5/1973 | Biskis |
| 3,830,676 | A | 8/1974 | Elkins |
| 3,867,939 | A | 2/1975 | Moore et al. |
| 3,900,035 | A | 8/1975 | Welch et al. |
| 3,927,671 | A | 12/1975 | Chittenden et al. |
| 3,945,617 | A | 3/1976 | Callery |
| 3,995,621 | A | 12/1976 | Fletcher et al. |
| 4,059,293 | A | 11/1977 | Sipler |
| 4,092,982 | A | 6/1978 | Salem |
| 4,108,146 | A | 8/1978 | Golden |
| 4,114,620 | A | 9/1978 | Moore et al. |
| 4,118,946 | A | 10/1978 | Tubin |
| 4,149,541 | A | 4/1979 | Gammons et al. |
| 4,154,245 | A | 5/1979 | Daily |
| 4,161,210 | A | 7/1979 | Reid et al. |
| 4,195,631 | A | 4/1980 | Baucom |
| 4,311,022 | A | 1/1982 | Hall |
| 4,444,727 | A | 4/1984 | Yanagihara et al. |
| 4,508,123 | A | 4/1985 | Wyatt et al. |
| 4,580,408 | A | 4/1986 | Stuebner |
| 4,753,241 | A | 6/1988 | Brannigan et al. |
| 4,834,705 | A | 5/1989 | Vaillancourt |
| 4,846,176 | A | 7/1989 | Golden |
| 4,867,748 | A | 9/1989 | Samuelsen |
| 4,884,304 | A | 12/1989 | Elkins |
| 4,886,063 | A | 12/1989 | Crews |
| 4,908,248 | A | 3/1990 | Nakashima et al. |
| 4,919,134 | A | 4/1990 | Streeter |
| 4,962,761 | A | 10/1990 | Golden |
| 4,971,056 | A | 11/1990 | Seacord |
| 4,981,135 | A | 1/1991 | Hardy |
| 4,989,607 | A | 2/1991 | Keusch et al. |
| 5,000,252 | A | 3/1991 | Faghri |
| 5,005,374 | A | 4/1991 | Spitler |
| 5,050,596 | A | 9/1991 | Walasek et al. |
| 5,062,414 | A | 11/1991 | Grim |
| 5,072,875 | A | 12/1991 | Zacoi |
| 5,090,409 | A | 2/1992 | Genis |
| 5,097,829 | A | 3/1992 | Quisenberry |
| 5,111,668 | A | 5/1992 | Parrish et al. |
| 5,113,666 | A | 5/1992 | Parrish et al. |
| 5,133,348 | A | 7/1992 | Mayn |
| 5,146,625 | A | 9/1992 | Steele et al. |
| 5,154,706 | A | 10/1992 | Cartmell et al. |
| 5,190,032 | A | 3/1993 | Zacoi |
| 5,265,669 | A | 11/1993 | Schneider |
| 5,268,022 | A | 12/1993 | Garrett et al. |
| 5,289,695 | A | 3/1994 | Parrish et al. |
| 5,300,103 | A | 4/1994 | Stempel et al. |
| 5,304,213 | A | 4/1994 | Berke et al. |
| 5,304,216 | A | 4/1994 | Wallace |
| 5,320,164 | A | 6/1994 | Szczesuil et al. |
| 5,329,638 | A | 7/1994 | Hansen et al. |
| 5,383,919 | A | 1/1995 | Kelly et al. |
| 5,393,462 | A | 2/1995 | Avery |
| 5,405,366 | A | 4/1995 | Fox et al. |
| 5,407,421 | A | 4/1995 | Goldsmith |
| 5,409,500 | A | 4/1995 | Dyrek |
| 5,411,541 | A | 5/1995 | Bell et al. |
| 5,423,751 | A | 6/1995 | Harrison et al. |
| 5,431,622 | A | 7/1995 | Pyrozyk et al. |
| 5,437,673 | A | 8/1995 | Baust et al. |
| 5,456,701 | A | 10/1995 | Stout |
| 5,466,250 | A | 11/1995 | Johnson, Jr. et al. |
| 5,470,353 | A | 11/1995 | Jensen |
| 5,476,489 | A | 12/1995 | Koewler |
| 5,484,448 | A | 1/1996 | Steele et al. |
| 5,486,207 | A | 1/1996 | Mahawili |
| 5,514,169 | A | 5/1996 | Dickerhoff et al. |
| 5,545,194 | A | 8/1996 | Augustine |
| 5,566,413 | A | 10/1996 | Webb et al. |
| 5,605,144 | A | 2/1997 | Simmons et al. |
| 5,609,620 | A | 3/1997 | Daily |
| 5,620,482 | A | 4/1997 | Augustine et al. |
| 5,624,477 | A | 4/1997 | Armond |
| 5,634,940 | A | 6/1997 | Panyard |
| 5,640,728 | A | 6/1997 | Graebe |
| 5,645,855 | A | 7/1997 | Lorenz |
| 5,658,325 | A | 8/1997 | Augustine |
| 5,662,695 | A | 9/1997 | Mason et al. |
| 5,683,439 | A | 11/1997 | Jensen |
| 5,720,774 | A | 2/1998 | Glucksman |
| 5,733,318 | A | 3/1998 | Augustine |
| 5,755,755 | A | 5/1998 | Panyard |
| 5,785,716 | A | 7/1998 | Bayron et al. |
| 5,806,335 | A | 9/1998 | Herbert et al. |
| 5,824,025 | A | 10/1998 | Augustine |
| 5,837,002 | A | 11/1998 | Augustine et al. |
| 5,840,080 | A | 11/1998 | Der Ovanesian |
| 5,843,145 | A | 12/1998 | Brink |
| 5,871,526 | A | 2/1999 | Gibbs et al. |
| 5,879,378 | A | 3/1999 | Usui |
| 5,887,437 | A | 3/1999 | Maxim |
| 5,913,849 | A | 6/1999 | Sundstrom et al. |
| 5,947,914 | A | 9/1999 | Augustine |
| 5,948,012 | A | 9/1999 | Mahaffey et al. |
| 5,968,000 | A | 10/1999 | Harrison et al. |
| 5,986,163 | A | 11/1999 | Augustine |
| 5,989,285 | A | 11/1999 | DeVilbiss et al. |
| 6,010,528 | A | 1/2000 | Augustine et al. |
| 6,019,783 | A | 2/2000 | Philips et al. |
| 6,030,412 | A | 2/2000 | Klatz et al. |
| 6,047,106 | A | 4/2000 | Salyer |
| 6,074,415 | A | 6/2000 | Der Ovanesian |
| 6,083,256 | A | 7/2000 | Der Ovanesian |
| 6,083,418 | A | 7/2000 | Czarnecki et al. |
| 6,117,164 | A | 9/2000 | Gildersleeve et al. |
| 6,176,869 | B1 | 1/2001 | Mason et al. |
| 6,176,870 | B1 | 1/2001 | Augustine |
| 6,185,744 | B1 | 2/2001 | Poholski |
| 6,188,930 | B1 | 2/2001 | Carson |
| 6,189,149 | B1 | 2/2001 | Allen |
| 6,189,550 | B1 | 2/2001 | Stickel et al. |
| 6,197,045 | B1 | 3/2001 | Carson |
| 6,234,538 | B1 | 5/2001 | Lauer |
| 6,238,427 | B1 | 5/2001 | Matta |
| 6,241,715 | B1 | 6/2001 | Houser et al. |
| 6,255,552 | B1 | 7/2001 | Cummings et al. |
| 6,257,011 | B1 | 7/2001 | Siman-Tov et al. |
| 6,290,716 | B1 | 9/2001 | Augustine |
| 6,336,935 | B1 | 1/2002 | Davis et al. |
| 6,349,560 | B1 | 2/2002 | Maier-Laxhuber et al. |
| 6,352,550 | B1 | 3/2002 | Gildersleeve et al. |
| 6,364,937 | B1 | 4/2002 | McMahon |
| 6,371,976 | B1 | 4/2002 | Vrzalik et al. |
| 6,375,674 | B1 | 4/2002 | Carson |
| 6,389,839 | B1 | 5/2002 | Sabin |
| 6,436,130 | B1 | 8/2002 | Philips et al. |
| 6,451,036 | B1 | 9/2002 | Heitzmann et al. |
| 6,454,792 | B1 | 9/2002 | Noda et al. |
| 6,461,379 | B1 | 10/2002 | Carson et al. |
| 6,463,212 | B1 | 10/2002 | Salyer |
| 6,503,297 | B1 | 1/2003 | Lu et al. |
| 6,508,831 | B1 | 1/2003 | Kushnir |

(56) References Cited

U.S. PATENT DOCUMENTS

| | | | |
|---|---|---|---|
| 6,508,859 | B1 | 1/2003 | Zia et al. |
| 6,511,501 | B1 | 1/2003 | Augustine et al. |
| 6,511,502 | B2 | 1/2003 | Fletcher |
| 6,517,510 | B1 | 2/2003 | Stewart et al. |
| D471,987 | S | 3/2003 | Hoglund et al. |
| D472,322 | S | 3/2003 | Hoglund et al. |
| 6,551,348 | B1 | 4/2003 | Blalock et al. |
| D474,544 | S | 5/2003 | Hoglund et al. |
| 6,559,096 | B1 | 5/2003 | Smith et al. |
| 6,584,797 | B1 | 7/2003 | Smith et al. |
| 6,589,270 | B2 | 7/2003 | Augustine |
| 6,591,630 | B2 | 7/2003 | Smith et al. |
| 6,601,404 | B1 | 8/2003 | Roderick |
| 6,613,030 | B1 | 9/2003 | Coles et al. |
| 6,620,187 | B2 | 9/2003 | Carson et al. |
| 6,620,188 | B1 | 9/2003 | Ginsburg et al. |
| 6,645,232 | B2 | 11/2003 | Carson |
| 6,648,905 | B2 | 11/2003 | Hoglund et al. |
| 6,653,607 | B2 | 11/2003 | Ellis et al. |
| D483,125 | S | 12/2003 | Hoglund et al. |
| 6,660,027 | B2 | 12/2003 | Gruszecki et al. |
| 6,669,715 | B2 | 12/2003 | Hoglund et al. |
| 6,682,525 | B2 | 1/2004 | Lalonde et al. |
| D487,147 | S | 2/2004 | Ellingboe et al. |
| D487,148 | S | 2/2004 | Ellingboe et al. |
| 6,688,132 | B2 | 2/2004 | Smith et al. |
| 6,692,518 | B2 | 2/2004 | Carson |
| 6,699,267 | B2 | 3/2004 | Voorhees et al. |
| 6,701,724 | B2 | 3/2004 | Smith et al. |
| 6,743,250 | B2 | 6/2004 | Renfro |
| 6,755,801 | B2 | 6/2004 | Utterberg et al. |
| 6,755,852 | B2 | 6/2004 | Lachenbruch et al. |
| D492,773 | S | 7/2004 | Ellingboe et al. |
| 6,770,848 | B2 | 8/2004 | Haas et al. |
| 6,799,063 | B2 | 9/2004 | Carson |
| 6,800,087 | B2 | 10/2004 | Papay et al. |
| 6,802,855 | B2 | 10/2004 | Ellingboe et al. |
| 6,802,885 | B2 | 10/2004 | Luk et al. |
| 6,818,012 | B2 | 11/2004 | Ellingboe |
| 6,827,728 | B2 | 12/2004 | Ellingboe et al. |
| 6,846,322 | B2 | 1/2005 | Kane et al. |
| 6,858,068 | B2 | 2/2005 | Smith et al. |
| 6,878,156 | B1 | 4/2005 | Noda |
| 6,893,453 | B2 | 5/2005 | Agarwal et al. |
| 6,904,956 | B2 | 6/2005 | Noel |
| 6,909,074 | B1 | 6/2005 | Bradley |
| 6,921,198 | B2 | 7/2005 | Gruszecki et al. |
| 6,931,875 | B1 | 8/2005 | Allen et al. |
| 6,942,644 | B2 | 9/2005 | Worthen |
| 6,960,243 | B1 | 11/2005 | Smith et al. |
| 6,968,711 | B2 | 11/2005 | Smith et al. |
| 6,969,399 | B2 | 11/2005 | Schock et al. |
| 7,008,445 | B2 | 3/2006 | Lennox |
| 7,022,099 | B2 | 4/2006 | Litzie et al. |
| 7,044,960 | B2 | 5/2006 | Voorhees et al. |
| 7,052,509 | B2 | 5/2006 | Lennox et al. |
| 7,055,575 | B2 | 6/2006 | Noel |
| 7,056,335 | B2 | 6/2006 | Agarwal et al. |
| 7,063,718 | B2 | 6/2006 | Dobak, III |
| 7,077,858 | B2 | 7/2006 | Fletcher et al. |
| 7,097,657 | B2 | 8/2006 | Noda et al. |
| 7,101,389 | B1 | 9/2006 | Augustine et al. |
| 7,122,047 | B2 | 10/2006 | Grahn et al. |
| 7,160,316 | B2 | 1/2007 | Hamilton et al. |
| 7,172,586 | B1 | 2/2007 | Dae et al. |
| 7,240,720 | B2 | 7/2007 | Noel |
| 7,303,554 | B2 | 12/2007 | Lalonde et al. |
| 7,303,579 | B2 | 12/2007 | Schock et al. |
| 7,338,516 | B2 | 3/2008 | Quincy, III et al. |
| 7,361,186 | B2 | 4/2008 | Voorhees et al. |
| 7,377,935 | B2 | 5/2008 | Schock et al. |
| 7,507,250 | B2 | 3/2009 | Lennox |
| 7,517,360 | B2 | 4/2009 | Frey et al. |
| RE40,815 | E | 6/2009 | Kudaravalli et al. |
| 7,547,320 | B2 | 6/2009 | Schook et al. |
| RE40,868 | E | 8/2009 | Ryba et al. |
| 7,621,944 | B2 | 11/2009 | Wilson et al. |
| 7,621,945 | B2 | 11/2009 | Lennox et al. |
| 7,666,213 | B2 | 2/2010 | Freedman, Jr. et al. |
| 7,678,716 | B2 | 3/2010 | Yahiaoui et al. |
| 7,686,840 | B2 | 3/2010 | Quincy, III et al. |
| 7,727,228 | B2 | 6/2010 | Abboud et al. |
| 7,731,739 | B2 | 6/2010 | Schock et al. |
| 7,744,640 | B1 | 6/2010 | Faries, Jr. et al. |
| 7,749,261 | B2 | 7/2010 | Hansen et al. |
| 7,763,061 | B2 | 7/2010 | Schorr et al. |
| 7,771,461 | B2 | 8/2010 | Schock et al. |
| 7,784,304 | B2 | 8/2010 | Trinh et al. |
| 7,799,063 | B2 | 9/2010 | Ingram et al. |
| 7,827,815 | B2 | 11/2010 | Carson et al. |
| 7,867,266 | B2 | 1/2011 | Collins |
| 7,892,269 | B2 | 2/2011 | Collins et al. |
| 7,896,910 | B2 | 3/2011 | Schirrmacher et al. |
| 7,918,243 | B2 | 4/2011 | Diodati et al. |
| 8,047,010 | B2 | 11/2011 | Carson et al. |
| 8,052,624 | B2 | 11/2011 | Buchanan et al. |
| 8,066,752 | B2 | 11/2011 | Hamilton et al. |
| 8,182,521 | B2 | 5/2012 | Kane et al. |
| 8,187,697 | B2 | 5/2012 | Quincy, III et al. |
| 8,216,163 | B2 | 7/2012 | Edelman |
| 8,283,602 | B2 | 10/2012 | Augustine et al. |
| 8,454,671 | B2 | 6/2013 | Lennox et al. |
| D685,916 | S | 7/2013 | Hoglund |
| 8,491,644 | B1 | 7/2013 | Carson et al. |
| 8,597,217 | B2 | 12/2013 | Lowe et al. |
| 8,597,339 | B2 | 12/2013 | Augustine et al. |
| 8,603,150 | B2 | 12/2013 | Kane et al. |
| 8,632,576 | B2 | 1/2014 | Quisenberry |
| 8,647,374 | B2 | 2/2014 | Koewler |
| 8,715,330 | B2 | 5/2014 | Lowe et al. |
| 8,778,119 | B2 | 7/2014 | Starr et al. |
| 8,808,344 | B2 | 8/2014 | Scott et al. |
| 8,840,581 | B2 | 9/2014 | McGill et al. |
| 9,034,458 | B2 | 5/2015 | Li |
| 9,078,742 | B2 | 7/2015 | Quincy et al. |
| 9,089,462 | B1 | 7/2015 | Lafleche |
| 9,211,358 | B2 | 12/2015 | Sinko et al. |
| 9,278,024 | B2 | 3/2016 | Scott et al. |
| 9,333,112 | B2 | 5/2016 | Carson |
| 9,433,527 | B2 | 9/2016 | Varga et al. |
| 9,552,706 | B2 | 1/2017 | Schneider, II et al. |
| 9,566,185 | B2 | 2/2017 | Carson et al. |
| 9,622,907 | B2 | 4/2017 | Carson et al. |
| 9,642,404 | B2 | 5/2017 | Giles et al. |
| 9,687,386 | B2 | 6/2017 | Carson |
| 9,763,823 | B2 | 9/2017 | Voorhees et al. |
| 9,907,889 | B2 | 3/2018 | Locke et al. |
| 10,010,452 | B2 | 7/2018 | Wenske et al. |
| 10,123,902 | B2 | 11/2018 | Carson et al. |
| 10,220,198 | B2 | 3/2019 | Fuchs et al. |
| 10,258,501 | B2 | 4/2019 | Carson |
| 10,376,412 | B2 | 8/2019 | Brienza et al. |
| 10,441,458 | B2 | 10/2019 | Voorhees et al. |
| 10,441,707 | B2 | 10/2019 | Voorhees et al. |
| 10,548,778 | B2 | 2/2020 | Hassenpflug et al. |
| 10,610,424 | B1 | 4/2020 | Hoover |
| D887,426 | S | 6/2020 | Matsushita |
| 10,912,672 | B1 | 2/2021 | Jones et al. |
| D922,424 | S | 6/2021 | Frueh et al. |
| D925,574 | S | 7/2021 | Beko |
| D928,188 | S | 8/2021 | Giannino et al. |
| 11,173,071 | B1 | 11/2021 | Tawil et al. |
| D939,550 | S | 12/2021 | Miyai et al. |
| 11,234,859 | B2 | 2/2022 | Voorhees et al. |
| D947,216 | S | 3/2022 | Leininger |
| 11,285,039 | B2 | 3/2022 | Steele et al. |
| D948,534 | S | 4/2022 | Bessette et al. |
| D952,666 | S | 5/2022 | Sajan |
| D959,475 | S | 8/2022 | Norman |
| D960,191 | S | 8/2022 | Feit et al. |
| D973,067 | S | 12/2022 | Oh et al. |
| 11,975,123 | B2 | 5/2024 | Appel et al. |
| 12,193,968 | B2 | 1/2025 | Voorhees et al. |
| 2001/0034545 | A1 | 10/2001 | Elkins |

(56) References Cited

U.S. PATENT DOCUMENTS

| | | | |
|---|---|---|---|
| 2001/0039439 | A1 | 11/2001 | Elkins et al. |
| 2002/0007203 | A1 | 1/2002 | Gilmartin et al. |
| 2002/0015689 | A1 | 2/2002 | Munro et al. |
| 2002/0019657 | A1 | 2/2002 | Elkins |
| 2002/0107558 | A1 | 8/2002 | Clifton et al. |
| 2002/0111657 | A1 | 8/2002 | Dae et al. |
| 2002/0138121 | A1 | 9/2002 | Fox |
| 2002/0161419 | A1 | 10/2002 | Carson et al. |
| 2003/0074038 | A1 | 4/2003 | Gruszecki et al. |
| 2003/0078638 | A1 | 4/2003 | Voorhees et al. |
| 2003/0078639 | A1 | 4/2003 | Carson |
| 2003/0078640 | A1 | 4/2003 | Carson et al. |
| 2003/0109911 | A1 | 6/2003 | Lachenbruch et al. |
| 2003/0114903 | A1 | 6/2003 | Ellingboe |
| 2003/0135252 | A1 | 7/2003 | MacHold et al. |
| 2003/0149359 | A1 | 8/2003 | Smith |
| 2003/0149461 | A1 | 8/2003 | Johnson |
| 2003/0150232 | A1 | 8/2003 | Brudnicki |
| 2003/0163179 | A1 | 8/2003 | Hoglund et al. |
| 2003/0163180 | A1 | 8/2003 | Hoglund et al. |
| 2003/0163183 | A1 | 8/2003 | Carson |
| 2003/0163185 | A1 | 8/2003 | Carson |
| 2003/0212416 | A1 | 11/2003 | Cinelli et al. |
| 2004/0030372 | A1 | 2/2004 | Ellingboe et al. |
| 2004/0030373 | A1 | 2/2004 | Ellingboe et al. |
| 2004/0059212 | A1 | 3/2004 | Abreu |
| 2004/0064170 | A1 | 4/2004 | Radons et al. |
| 2004/0064171 | A1 | 4/2004 | Briscoe et al. |
| 2004/0073280 | A1 | 4/2004 | Dae et al. |
| 2004/0082886 | A1 | 4/2004 | Timpson |
| 2004/0087606 | A1 | 5/2004 | Voorhees et al. |
| 2004/0133253 | A1 | 7/2004 | Grahn et al. |
| 2004/0158303 | A1 | 8/2004 | Lennox et al. |
| 2004/0225341 | A1 | 11/2004 | Schock et al. |
| 2004/0243122 | A1 | 12/2004 | Auth et al. |
| 2004/0252750 | A1 | 12/2004 | Gruszecki et al. |
| 2004/0255362 | A1 | 12/2004 | Soerens et al. |
| 2004/0260369 | A1 | 12/2004 | Schock et al. |
| 2004/0267339 | A1 | 12/2004 | Yon et al. |
| 2005/0028551 | A1 | 2/2005 | Noda et al. |
| 2005/0060012 | A1 | 3/2005 | Voorhees et al. |
| 2005/0065583 | A1 | 3/2005 | Voorhees et al. |
| 2005/0096714 | A1 | 5/2005 | Freedman et al. |
| 2005/0177212 | A1 | 8/2005 | Njemanze |
| 2005/0187502 | A1 | 8/2005 | Krempel et al. |
| 2005/0244629 | A1 | 11/2005 | Usui et al. |
| 2005/0288749 | A1 | 12/2005 | Lachenbruch |
| 2006/0024053 | A1 | 2/2006 | Grant |
| 2006/0030916 | A1 | 2/2006 | Lennox |
| 2006/0036304 | A1 | 2/2006 | Cordani et al. |
| 2006/0058858 | A1 | 3/2006 | Smith |
| 2006/0069418 | A1 | 3/2006 | Schock et al. |
| 2006/0074469 | A1 | 4/2006 | Lennox et al. |
| 2006/0122673 | A1 | 6/2006 | Callister et al. |
| 2006/0124141 | A1 | 6/2006 | Dobak |
| 2006/0136023 | A1 | 6/2006 | Dobak |
| 2006/0161232 | A1 | 7/2006 | Kasza et al. |
| 2006/0190066 | A1 | 8/2006 | Worthen |
| 2006/0235114 | A1 | 10/2006 | Kitazono et al. |
| 2006/0247744 | A1 | 11/2006 | Nest et al. |
| 2006/0276089 | A1 | 12/2006 | Amarasinghe et al. |
| 2006/0287697 | A1 | 12/2006 | Lennox |
| 2006/0293734 | A1 | 12/2006 | Scott et al. |
| 2007/0016270 | A1 | 1/2007 | Stelea et al. |
| 2007/0043409 | A1 | 2/2007 | Brian et al. |
| 2007/0049997 | A1 | 3/2007 | Fields et al. |
| 2007/0054122 | A1 | 3/2007 | Paisner et al. |
| 2007/0068931 | A1 | 3/2007 | Augustine et al. |
| 2007/0073368 | A1 | 3/2007 | Cazzini et al. |
| 2007/0100404 | A1 | 5/2007 | Ko et al. |
| 2007/0173735 | A1 | 7/2007 | Callister et al. |
| 2007/0213793 | A1 | 9/2007 | Hayes |
| 2007/0225782 | A1 | 9/2007 | Taylor |
| 2007/0244475 | A1 | 10/2007 | Carson et al. |
| 2007/0270925 | A1 | 11/2007 | Levinson |
| 2008/0027523 | A1 | 1/2008 | Behringer et al. |
| 2008/0046046 | A1 | 2/2008 | Ginsburg |
| 2008/0114431 | A1 | 5/2008 | Ginsburg |
| 2008/0147152 | A1 | 6/2008 | Quincy et al. |
| 2008/0249524 | A1 | 10/2008 | Dunning |
| 2008/0255644 | A1 | 10/2008 | Carson |
| 2008/0269852 | A1* | 10/2008 | Lennox ..................... A61F 7/02 607/104 |
| 2008/0275534 | A1 | 11/2008 | Noel |
| 2009/0018504 | A1 | 1/2009 | Pile-Spellman et al. |
| 2009/0043366 | A1 | 2/2009 | Dae |
| 2009/0066079 | A1 | 3/2009 | Miros et al. |
| 2009/0088825 | A1 | 4/2009 | Pta |
| 2009/0099629 | A1 | 4/2009 | Carson et al. |
| 2009/0131835 | A1 | 5/2009 | Voorhees et al. |
| 2009/0149925 | A1 | 6/2009 | MacDonald et al. |
| 2009/0157000 | A1 | 6/2009 | Waller |
| 2009/0177184 | A1 | 7/2009 | Christensen et al. |
| 2009/0182400 | A1 | 7/2009 | Dae et al. |
| 2009/0228082 | A1 | 9/2009 | Ross et al. |
| 2009/0250367 | A1 | 10/2009 | Murdoch et al. |
| 2009/0280182 | A1 | 11/2009 | Beck et al. |
| 2009/0287283 | A1 | 11/2009 | Biser et al. |
| 2009/0299287 | A1 | 12/2009 | Carson et al. |
| 2009/0312823 | A1 | 12/2009 | Patience et al. |
| 2009/0326619 | A1 | 12/2009 | Kagan |
| 2010/0016933 | A1 | 1/2010 | Chen et al. |
| 2010/0137951 | A1 | 6/2010 | Lennox et al. |
| 2010/0168825 | A1 | 7/2010 | Barbknecht |
| 2010/0198122 | A1 | 8/2010 | Freund |
| 2010/0198320 | A1 | 8/2010 | Pierre et al. |
| 2010/0204765 | A1 | 8/2010 | Hall et al. |
| 2010/0217260 | A1 | 8/2010 | Aramayo |
| 2010/0241073 | A1 | 9/2010 | Andersen et al. |
| 2010/0312160 | A1 | 12/2010 | Creighton et al. |
| 2010/0312202 | A1 | 12/2010 | Henley et al. |
| 2011/0021960 | A1 | 1/2011 | Filtvedt et al. |
| 2011/0029051 | A1 | 2/2011 | Ross |
| 2011/0045056 | A1 | 2/2011 | Munro et al. |
| 2011/0098792 | A1 | 4/2011 | Lowe et al. |
| 2011/0098793 | A1 | 4/2011 | Lowe et al. |
| 2011/0125238 | A1 | 5/2011 | Nofzinger |
| 2011/0152982 | A1 | 6/2011 | Richardson |
| 2011/0166633 | A1 | 7/2011 | Stull |
| 2011/0172749 | A1 | 7/2011 | Christensen et al. |
| 2011/0172750 | A1 | 7/2011 | Cassidy et al. |
| 2011/0306972 | A1 | 12/2011 | Widenhouse et al. |
| 2011/0307040 | A1 | 12/2011 | Peterson |
| 2011/0308781 | A1 | 12/2011 | O'Riordan et al. |
| 2011/0313497 | A1 | 12/2011 | Mcfarlane |
| 2012/0046720 | A1 | 2/2012 | Ishizaki |
| 2012/0065715 | A1 | 3/2012 | Carson |
| 2012/0080031 | A1 | 4/2012 | Belson |
| 2012/0095536 | A1 | 4/2012 | Machold et al. |
| 2012/0172774 | A1 | 7/2012 | Lowe et al. |
| 2012/0185021 | A1 | 7/2012 | Johnson et al. |
| 2012/0191035 | A1 | 7/2012 | Stephan |
| 2012/0204881 | A1 | 8/2012 | Davidson et al. |
| 2012/0220960 | A1 | 8/2012 | Ruland |
| 2012/0288848 | A1 | 11/2012 | Latham et al. |
| 2013/0006335 | A1 | 1/2013 | Lowe |
| 2013/0023808 | A1 | 1/2013 | Brown et al. |
| 2013/0116760 | A1 | 5/2013 | Carson et al. |
| 2013/0138185 | A1 | 5/2013 | Paxman et al. |
| 2013/0190667 | A1 | 7/2013 | Kane et al. |
| 2013/0238042 | A1 | 9/2013 | Gildersleeve et al. |
| 2013/0238043 | A1 | 9/2013 | Beardall et al. |
| 2013/0310725 | A1 | 11/2013 | Jerrells et al. |
| 2014/0039451 | A1 | 2/2014 | Bangera et al. |
| 2014/0046411 | A1 | 2/2014 | Elkins et al. |
| 2014/0172050 | A1 | 6/2014 | Dabrowiak |
| 2014/0214138 | A1 | 7/2014 | Voorhees et al. |
| 2014/0222121 | A1 | 8/2014 | Spence et al. |
| 2014/0228717 | A1 | 8/2014 | Parish et al. |
| 2014/0228918 | A1 | 8/2014 | Brienza et al. |
| 2014/0276253 | A1 | 9/2014 | Varga et al. |
| 2014/0277301 | A1 | 9/2014 | Varga et al. |
| 2014/0288621 | A1 | 9/2014 | Efremkin |
| 2014/0316494 | A1 | 10/2014 | Augustine et al. |

(56) References Cited

U.S. PATENT DOCUMENTS

| | | | | |
|---|---|---|---|---|
| 2014/0343639 | A1 | 11/2014 | Hopper et al. | |
| 2015/0025606 | A1 | 1/2015 | Davis | |
| 2015/0051673 | A1 | 2/2015 | Rivas Tapia | |
| 2015/0119963 | A1* | 4/2015 | Cosse | F25D 5/02 126/263.08 |
| 2015/0173942 | A1 | 6/2015 | Whitely | |
| 2015/0209174 | A1 | 7/2015 | Abreu | |
| 2015/0209192 | A1 | 7/2015 | Manion et al. | |
| 2015/0223972 | A1 | 8/2015 | Dabrowiak | |
| 2015/0230973 | A1 | 8/2015 | Dabrowiak et al. | |
| 2015/0231009 | A1 | 8/2015 | Lewis | |
| 2015/0250643 | A1 | 9/2015 | Paradis | |
| 2015/0290042 | A1 | 10/2015 | Freer et al. | |
| 2015/0366703 | A1 | 12/2015 | Du | |
| 2015/0373781 | A1 | 12/2015 | Augustine et al. | |
| 2015/0374045 | A1 | 12/2015 | Codner et al. | |
| 2016/0008166 | A1 | 1/2016 | Voorhees et al. | |
| 2016/0022477 | A1 | 1/2016 | Schaefer et al. | |
| 2016/0038336 | A1 | 2/2016 | Hilton et al. | |
| 2016/0310316 | A1 | 10/2016 | Hixson, Jr. | |
| 2016/0324683 | A1 | 11/2016 | Carson | |
| 2017/0049618 | A1 | 2/2017 | Ward et al. | |
| 2017/0135855 | A1 | 5/2017 | Stefan et al. | |
| 2017/0151087 | A1 | 6/2017 | Carson et al. | |
| 2017/0189225 | A1 | 7/2017 | Voorhees et al. | |
| 2017/0209305 | A1 | 7/2017 | Kaforey et al. | |
| 2017/0224528 | A1 | 8/2017 | Berg et al. | |
| 2017/0246029 | A1 | 8/2017 | Clark | |
| 2017/0246031 | A1 | 8/2017 | Benyaminpour et al. | |
| 2017/0246374 | A1 | 8/2017 | Voorhees et al. | |
| 2017/0348144 | A1 | 12/2017 | Taylor et al. | |
| 2017/0348145 | A1 | 12/2017 | Voorhees et al. | |
| 2017/0354534 | A1 | 12/2017 | Paradis et al. | |
| 2018/0000255 | A1 | 1/2018 | Youngblood et al. | |
| 2018/0014967 | A1 | 1/2018 | Taylor | |
| 2018/0042762 | A1 | 2/2018 | Galer | |
| 2018/0042763 | A1 | 2/2018 | Galer et al. | |
| 2018/0056097 | A1 | 3/2018 | Provencal | |
| 2018/0064594 | A1 | 3/2018 | Finch, Jr. et al. | |
| 2018/0140407 | A1 | 5/2018 | Yoskowitz | |
| 2018/0207024 | A1 | 7/2018 | Dabrowiak et al. | |
| 2018/0214297 | A1 | 8/2018 | Hughett et al. | |
| 2018/0214302 | A1 | 8/2018 | Dabrowiak et al. | |
| 2018/0263677 | A1 | 9/2018 | Hilton et al. | |
| 2018/0263748 | A1 | 9/2018 | Quinn | |
| 2018/0295980 | A1 | 10/2018 | Boersma et al. | |
| 2018/0376539 | A1 | 12/2018 | Augustine et al. | |
| 2019/0083322 | A1 | 3/2019 | Huang et al. | |
| 2019/0085644 | A1 | 3/2019 | Ames et al. | |
| 2019/0099288 | A1 | 4/2019 | Vergara et al. | |
| 2019/0117446 | A1 | 4/2019 | Carson et al. | |
| 2019/0192337 | A1 | 6/2019 | Taylor et al. | |
| 2019/0201574 | A1 | 7/2019 | Delury et al. | |
| 2019/0262169 | A1 | 8/2019 | Vergara et al. | |
| 2019/0328576 | A1 | 10/2019 | Lowe et al. | |
| 2019/0331277 | A1 | 10/2019 | Vachon | |
| 2020/0001022 | A1 | 1/2020 | Landy, III et al. | |
| 2020/0071051 | A1 | 3/2020 | Lewis | |
| 2020/0129326 | A1 | 4/2020 | Sinha et al. | |
| 2020/0155341 | A1 | 5/2020 | Voorhees et al. | |
| 2020/0214471 | A1 | 7/2020 | Paperno | |
| 2020/0246180 | A1 | 8/2020 | Liang et al. | |
| 2020/0289361 | A1 | 9/2020 | Tian et al. | |
| 2020/0345971 | A1 | 11/2020 | Schirm et al. | |
| 2020/0405530 | A1 | 12/2020 | Taylor et al. | |
| 2021/0060230 | A1 | 3/2021 | Hopper et al. | |
| 2021/0123641 | A1 | 4/2021 | Monazami et al. | |
| 2022/0087874 | A1 | 3/2022 | Schneider et al. | |
| 2022/0151821 | A1 | 5/2022 | Voorhees et al. | |
| 2022/0192865 | A1 | 6/2022 | Hughett, Sr. et al. | |
| 2022/0192867 | A1 | 6/2022 | Stich et al. | |
| 2022/0233344 | A1 | 7/2022 | Hoglund | |
| 2022/0233347 | A1 | 7/2022 | Canary et al. | |
| 2022/0265468 | A1 | 8/2022 | Xu et al. | |
| 2022/0280336 | A1 | 9/2022 | Smith et al. | |
| 2022/0287875 | A1 | 9/2022 | Minchew et al. | |
| 2022/0287876 | A1 | 9/2022 | Smith et al. | |
| 2022/0296413 | A1 | 9/2022 | Jones | |
| 2022/0296414 | A1 | 9/2022 | Bible et al. | |
| 2022/0304847 | A1 | 9/2022 | Kuroda et al. | |
| 2022/0313478 | A1 | 10/2022 | Johnston et al. | |
| 2022/0331153 | A1 | 10/2022 | Xie et al. | |
| 2022/0347009 | A1 | 11/2022 | Hughett, Sr. et al. | |
| 2022/0401259 | A1 | 12/2022 | Basciano et al. | |
| 2022/0406017 | A1 | 12/2022 | Wang et al. | |
| 2023/0000668 | A1 | 1/2023 | Walker et al. | |
| 2023/0009524 | A1 | 1/2023 | Johnston et al. | |
| 2023/0011631 | A1 | 1/2023 | Yin et al. | |
| 2023/0019048 | A1 | 1/2023 | Stich et al. | |
| 2023/0021245 | A1 | 1/2023 | Walker et al. | |
| 2023/0040583 | A1 | 2/2023 | Falis et al. | |
| 2023/0077318 | A9 | 3/2023 | Voorhees et al. | |
| 2023/0346630 | A1 | 11/2023 | Lowe et al. | |
| 2023/0414445 | A1 | 12/2023 | Sundar et al. | |
| 2024/0065884 | A1 | 2/2024 | Fallows et al. | |
| 2024/0082052 | A1 | 3/2024 | Cho et al. | |
| 2024/0091054 | A1 | 3/2024 | Boone-Worthman et al. | |
| 2024/0099878 | A1 | 3/2024 | Voorhees et al. | |
| 2024/0108497 | A1 | 4/2024 | Daw et al. | |
| 2024/0366422 | A1 | 11/2024 | Johnston et al. | |
| 2025/0032310 | A1 | 1/2025 | Stich et al. | |
| 2025/0041107 | A1 | 2/2025 | Walker et al. | |
| 2025/0110628 | A1 | 4/2025 | Litman et al. | |
| 2025/0134705 | A1 | 5/2025 | Stich et al. | |
| 2025/0143918 | A1 | 5/2025 | Voorhees et al. | |
| 2025/0161107 | A1 | 5/2025 | Stich et al. | |
| 2025/0198550 | A1 | 6/2025 | Johnston et al. | |
| 2025/0332025 | A1 | 10/2025 | Brooks et al. | |
| 2026/0026965 | A1 | 1/2026 | Xu et al. | |
| 2026/0102279 | A1 | 4/2026 | Canary et al. | |
| 2026/0174591 | A1 | 6/2026 | Johnston et al. | |

FOREIGN PATENT DOCUMENTS

| | | | |
|---|---|---|---|
| CA | 2729122 | A1 | 7/2002 |
| CA | 2193385 | C | 9/2006 |
| CN | 101389372 | B | 8/2012 |
| CN | 102746518 | A | 10/2012 |
| CN | 103939695 | B | 3/2016 |
| CN | 305928532 | | 7/2020 |
| CN | 111643265 | A | 9/2020 |
| CN | 306402573 | | 3/2021 |
| CN | 113230017 | A | 8/2021 |
| CN | 307690236 | | 11/2022 |
| CN | 309180016 | | 3/2025 |
| DE | 102014118510 | A1 | 6/2016 |
| EP | 0862901 | A1 | 9/1998 |
| EP | 1073388 | A1 | 2/2001 |
| EP | 1616543 | A2 | 1/2006 |
| EP | 1641503 | A2 | 4/2006 |
| EP | 1718894 | B1 | 7/2010 |
| EP | 2204150 | A1 | 7/2010 |
| EP | 2269546 | A1 | 1/2011 |
| GB | 2118440 | A | 11/1983 |
| IN | 102026596 | A | 4/2011 |
| JP | H09508045 | A | 8/1997 |
| JP | 2002534160 | A | 10/2002 |
| JP | 2007029638 | A | 2/2007 |
| JP | 2013248293 | A | 12/2013 |
| KR | 20110020420 | A | 3/2011 |
| NO | 2005117546 | A2 | 12/2005 |
| WO | 9807397 | A1 | 2/1998 |
| WO | 9831310 | A1 | 7/1998 |
| WO | 199944552 | A1 | 9/1999 |
| WO | 9953874 | A1 | 10/1999 |
| WO | 2000040185 | A1 | 7/2000 |
| WO | 2003086253 | A2 | 10/2003 |
| WO | 2004075949 | A2 | 9/2004 |
| WO | 2005028984 | A1 | 3/2005 |
| WO | 2007120677 | A2 | 10/2007 |
| WO | 2009090403 | A1 | 7/2009 |
| WO | 2009147413 | A1 | 12/2009 |
| WO | 2009148636 | A1 | 12/2009 |
| WO | 2012125916 | A2 | 9/2012 |

(56) References Cited

FOREIGN PATENT DOCUMENTS

| | | | |
|---|---|---|---|
| WO | 2012138980 | A2 | 10/2012 |
| WO | 2015084925 | A1 | 6/2015 |
| WO | 2016057119 | A1 | 4/2016 |
| WO | 2016123500 | A1 | 8/2016 |
| WO | 2017127768 | A1 | 7/2017 |
| WO | 2018075576 | A1 | 4/2018 |
| WO | 2022155130 | A1 | 7/2022 |
| WO | 2022155132 | A1 | 7/2022 |
| WO | 2022159513 | A1 | 7/2022 |
| WO | 2022159879 | A1 | 7/2022 |
| WO | 2022165068 | A1 | 8/2022 |
| WO | 2022235513 | A1 | 11/2022 |
| WO | 2023121674 | A1 | 6/2023 |
| WO | 2023140870 | A1 | 7/2023 |
| WO | 2023154050 | A1 | 8/2023 |
| WO | 2023229609 | A1 | 11/2023 |
| WO | 2026136069 | A1 | 6/2026 |

OTHER PUBLICATIONS

U.S. Appl. No. 17/848,074, filed Jun. 23, 2022 Advisory Action dated Jul. 9, 2024.
U.S. Appl. No. 17/848,074, filed Jun. 23, 2022 Final Office Action dated Apr. 26, 2024.
U.S. Appl. No. 18/536,087, filed Dec. 11, 2023 Non-Final Office Action dated Jun. 28, 2024.
All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).
Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).
Injection Tracker App, posted date unavailable [online], [retrieved Apr. 10, 2025]. Retrieved from internet, https://www.vladcristei.com/project_page_it. (Year: 2025).
U.S. Appl. No. 17/583,090, filed Jan. 24, 2022 Final Office Action dated Jul. 1, 2025.
U.S. Appl. No. 17/678,965, filed Feb. 23, 2022 Notice of Allowance dated Jun. 3, 2025.
U.S. Appl. No. 17/686,301, filed Mar. 3, 2022 Non-Final Office Action dated May 14, 2025.
U.S. Appl. No. 17/689,791, filed Mar. 8, 2022 Final Office Action dated May 21, 2025.
U.S. Appl. No. 17/690,908, filed Mar. 9, 2022 Final Office Action dated Jun. 24, 2025.
U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Final Office Action dated Jun. 15, 2025.
U.S. Appl. No. 17/723,210, filed Apr. 18, 2022 Final Office Action dated May 21, 2025.
U.S. Appl. No. 17/849,419, filed Jun. 24, 2022 Non-Final Office Action dated Jun. 13, 2025.
U.S. Appl. No. 17/857,997, filed Jul. 5, 2022 Non-Final Office Action dated Apr. 28, 2025.
U.S. Appl. No. 17/881,270, filed Aug. 4, 2022 Non-Final Office Action dated Apr. 28, 2025.
U.S. Appl. No. 29/939,277, filed Apr. 25, 2024 Non-Final Office Action dated May 13, 2025.
Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCT/US2022/026999 filed Apr. 29, 2022 International Search Report and Written Opinion dated Oct. 24, 2022.
PCTUS2022011971 filed Jan. 11, 2022 International Search Report and Written Opinion dated Apr. 21, 2022.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
U.S. Appl. No. 17/589,849, filed Jan. 31, 2022 Notice of Allowance dated Aug. 23, 2023.
U.S. Appl. No. 17/848,074, filed Jun. 23, 2022 Non-Final Office Action dated Nov. 30, 2023.
PCT/US2022/031428 filed May 27, 2022 International Search Report and Written Opinion dated Jan. 30, 2023.
U.S. Appl. No. 17/547,128, filed Dec. 9, 2021 Non-Final Office Action dated Feb. 10, 2025.
U.S. Appl. No. 17/552,309, filed Dec. 15, 2021 Non-Final Office Action dated Mar. 14, 2025.
U.S. Appl. No. 17/552,309, filed Dec. 15, 2021 Restriction Requirement dated Dec. 12, 2024.
U.S. Appl. No. 17/583,090, filed Jan. 24, 2022 Non-Final Office Action dated Feb. 13, 2025.
U.S. Appl. No. 17/584,101, filed Jan. 25, 2022 Non-Final Office Action dated Feb. 5, 2025.
U.S. Appl. No. 17/584,101, filed Jan. 25, 2022 Restriction Requirement dated Nov. 5, 2024.
U.S. Appl. No. 17/678,965, filed Feb. 23, 2022 Non-Final Office Action dated Feb. 12, 2025.
U.S. Appl. No. 17/686,301, filed Mar. 3, 2022 Advisory Action dated Apr. 4, 2025.
U.S. Appl. No. 17/686,301, filed Mar. 3, 2022 Final Office Action dated Jan. 29, 2025.
U.S. Appl. No. 17/689,791, filed Mar. 8, 2022 Non-Final Office Action dated Dec. 30, 2024.
U.S. Appl. No. 17/690,908, filed Mar. 9, 2022 Non-Final Office Action dated Dec. 18, 2024.
U.S. Appl. No. 17/691,990, filed Mar. 10, 2022 Non-Final Office Action dated Dec. 17, 2024.
U.S. Appl. No. 17/694,416, filed Mar. 14, 2022 Non-Final Office Action dated Jan. 22, 2025.
U.S. Appl. No. 17/694,416, filed Mar. 14, 2022 Restriction Requirement dated Nov. 8, 2024.
U.S. Appl. No. 17/700,216, filed Mar. 21, 2022 Non-Final Office Action dated Feb. 5, 2025.
U.S. Appl. No. 17/709,019, filed Mar. 30, 2022 Non-Final Office Action dated Dec. 31, 2024.
U.S. Appl. No. 17/723,210, filed Apr. 18, 2022 Non-Final Office Action dated Dec. 20, 2024.
U.S. Appl. No. 17/848,074, filed Jun. 23, 2022 Notice of Allowance dated Nov. 26, 2024.
U.S. Appl. No. 17/849,419, filed Jun. 24, 2022 Final Office Action dated Feb. 14, 2025.
U.S. Appl. No. 17/849,419, filed Jun. 24, 2022 Non-Final Office Action dated Nov. 8, 2024.
U.S. Appl. No. 17/857,997, filed Jul. 5, 2022 Restriction Requirement dated Feb. 12, 2025.
U.S. Appl. No. 17/859,995, filed Jul. 7, 2022 Non-Final Office Action dated Mar. 11, 2025.
U.S. Appl. No. 17/881,270, filed Aug. 4, 2022 Restriction Requirement dated Feb. 11, 2025.
Advantage Engineering, "Proper Use of Inhibited Propylene Glycol", Jun. 12, 2001, http://www.ttequip.com/knowledgelibrary/Proper%20Use%20Of%20Inh- ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g- us.edu/hbase/tables.thron.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).
PCT/US2015/045548 filed Aug. 17, 2015 International Search Report and Written Opinion dated Novemeber 24, 2015.

(56) References Cited

OTHER PUBLICATIONS

PCT/US2016/015688 filed Jan. 29, 2016 International Search Report and Written Opinion dated Apr. 1, 2016.
PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
Sevgi, M., et al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.
PCT/US2022/013569 filed Jan. 24, 2022 International Search Report and Written Opinion dated Aug. 29, 2022.
PCT/US2022/016020 filed Feb. 10, 2022 International Search Report and Written Opinion dated Oct. 31, 2022.
U.S. Appl. No. 17/547,128, filed Dec. 9, 2021 Restriction Requirement dated Sep. 5, 2024.
U.S. Appl. No. 17/583,090, filed Jan. 24, 2022 Restriction Requirement dated Sep. 6, 2024.
U.S. Appl. No. 17/686,301, filed Mar. 3, 2022 Non-Final Office Action dated Oct. 1, 2024.
U.S. Appl. No. 17/689,791, filed Mar. 8, 2022 Restriction Requirement dated Oct. 16, 2024.
U.S. Appl. No. 17/691,990, filed Mar. 10, 2022 Restriction Requirement dated Oct. 16, 2024.
U.S. Appl. No. 17/709,019, filed Mar. 30, 2022 Restriction Requirement dated Oct. 16, 2024.
U.S. Appl. No. 17/723,210, filed Apr. 18, 2022 Restriction Requirement dated Oct. 16, 2024.
U.S. Appl. No. 17/848,074, filed Jun. 23, 2022 Non-Final Office Action dated Aug. 15, 2024.
U.S. Appl. No. 18/536,087, filed Dec. 11, 2023 Notice of Allowance dated Aug. 29, 2024.
Lustig et al. "Solute Diffusion in Swollen Membranes. IX. Scaling Laws for Solute Diffusion in Gels", Journal of Applied Polymer Science, vol. 36, pp. 735-747 (Year: 1988).
U.S. Appl. No. 17/547,128, filed Dec. 9, 2021 Advisory Action dated Nov. 19, 2025.
U.S. Appl. No. 17/547,128, filed Dec. 9, 2021 Final Office Action dated Aug. 27, 2025.
U.S. Appl. No. 17/547,128, filed Dec. 9, 2021 Non-Final Office Action dated Dec. 29, 2025.
U.S. Appl. No. 17/552,309, filed Dec. 15, 2021 Advisory Action dated Oct. 2, 2025.
U.S. Appl. No. 17/552,309, filed Dec. 15, 2021 Final Office Action dated Jul. 30, 2025.
U.S. Appl. No. 17/552,309, filed Dec. 15, 2021 Non-Final Office Action dated Nov. 5, 2025.
U.S. Appl. No. 17/583,090, filed Jan. 24, 2022 Notice of Allowance dated Sep. 30, 2025.
U.S. Appl. No. 17/584,101, filed Jan. 25, 2022 Final Office Action dated Oct. 23, 2025.
U.S. Appl. No. 17/686,301, filed Mar. 3, 2022 Advisory Action dated Jan. 14, 2026.
U.S. Appl. No. 17/686,301, filed Mar. 3, 2022 Final Office Action dated Oct. 28, 2025.
U.S. Appl. No. 17/689,791, filed Mar. 8, 2022 Advisory Action dated Jul. 24, 2025.
U.S. Appl. No. 17/689,791, filed Mar. 8, 2022 Non-Final Office Action dated Nov. 5, 2025.
U.S. Appl. No. 17/690,908, filed Mar. 9, 2022 Advisory Action dated Sep. 3, 2025.
U.S. Appl. No. 17/690,908, filed Mar. 9, 2022 Non-Final Office Action dated Oct. 2, 2025.
U.S. Appl. No. 17/691,990, filed Mar. 10, 2022 Advisory Action dated Jul. 24, 2025.
U.S. Appl. No. 17/691,990, filed Mar. 10, 2022 Non-Final Office Action dated Aug. 28, 2025.
U.S. Appl. No. 17/694,416, filed Mar. 14, 2022 Advisory Action dated Aug. 20, 2025.
U.S. Appl. No. 17/694,416, filed Mar. 14, 2022 Non-Final Office Action dated Oct. 1, 2025.
U.S. Appl. No. 17/697,879, filed Mar. 17, 2022 Non-Final Office Action dated Sep. 30, 2025.
U.S. Appl. No. 17/700,216, filed Mar. 21, 2022 Advisory Action dated Oct. 9, 2025.
U.S. Appl. No. 17/700,216, filed Mar. 21, 2022 Non-Final Office Action dated Dec. 3, 2025.
U.S. Appl. No. 17/709,019, filed Mar. 30, 2022 Advisory Action dated Jul. 24, 2025.
U.S. Appl. No. 17/709,019, filed Mar. 30, 2022 Non-Final Office Action dated Nov. 19, 2025.
U.S. Appl. No. 17/723,210, filed Apr. 18, 2022 Advisory Action dated Jul. 31, 2025.
U.S. Appl. No. 17/723,210, filed Apr. 18, 2022 Non-Final Office Action dated Dec. 29, 2025.
U.S. Appl. No. 17/837,956, filed Jun. 10, 2022 Non-Final Office Action dated Nov. 3, 2025.
U.S. Appl. No. 17/848,039, filed Jun. 23, 2021 Non-Final Office Action dated Jul. 29, 2025.
U.S. Appl. No. 17/848,039, filed Jun. 23, 2022 Final Office Action dated Dec. 29, 2025.
U.S. Appl. No. 17/857,997, filed Jul. 5, 2022 Final Office Action dated Oct. 27, 2025.
U.S. Appl. No. 17/859,995, filed Jul. 7, 2022 Advisory Action dated Oct. 28, 2025.
U.S. Appl. No. 17/859,995, filed Jul. 7, 2022 Final Office Action dated Aug. 22, 2025.
U.S. Appl. No. 17/859,995, filed Jul. 7, 2022 Non-Final Office Action dated Dec. 23, 2025.
U.S. Appl. No. 17/881,270, filed Aug. 4, 2022 Advisory Action dated Jan. 14, 2026.
U.S. Appl. No. 17/881,270, filed Aug. 4, 2022 Final Office Action dated Oct. 27, 2025.
U.S. Appl. No. 18/272,026, filed Jul. 12, 2023 Non-Final Office Action dated Jul. 31, 2025.
U.S. Appl. No. 18/273,163, filed Jul. 19, 2023 Restriction Requirement dated Nov. 6, 2025.
U.S. Appl. No. 18/274,156, filed Jul. 25, 2023 Non-Final Office Action dated Oct. 1, 2025.
U.S. Appl. No. 18/274,436, filed Jul. 26, 2023 Non-Final Office Action dated Oct. 1, 2025.
U.S. Appl. No. 18/289,341, filed Nov. 2, 2023 Restriction Requirement dated Nov. 6, 2025.
U.S. Appl. No. 19/068,969, filed Mar. 3, 2025 Non-Final Office Action dated Dec. 29, 2025.
U.S. Appl. No. 29/939,277, filed Apr. 25, 2024 Restriction Requirement dated Oct. 2, 2025.
U.S. Appl. No. 17/547,128, filed Dec. 9, 2021 Final Office Action dated Apr. 6, 2026.
U.S. Appl. No. 17/686,301, filed Mar. 3, 2022 Non-Final Office Action dated Apr. 3, 2026.
U.S. Appl. No. 17/691,990, filed Mar. 10, 2022 Final Office Action dated Mar. 9, 2026.
U.S. Appl. No. 17/694,416, filed Mar. 14, 2022 Final Office Action dated Apr. 9, 2026.
U.S. Appl. No. 17/697,879, filed Mar. 17, 2022 Non-Final Office Action dated Mar. 26, 2026.
U.S. Appl. No. 17/837,956, filed Jun. 10, 2022 Final Office Action dated Feb. 24, 2026.
U.S. Appl. No. 17/848,039, filed Jun. 23, 2022 Notice of Allowance dated Apr. 13, 2026.

(56) References Cited

OTHER PUBLICATIONS

U.S. Appl. No. 17/849,419, filed Jun. 24, 2022 Notice of Allowance dated Jan. 29, 2026.
U.S. Appl. No. 18/272,026, filed Jul. 12, 2023 Notice of Allowance dated Mar. 27, 2026.
U.S. Appl. No. 18/272,332, filed Jul. 13, 2023 Non-Final Office Action dated Mar. 25, 2026.
U.S. Appl. No. 18/272,332, filed Jul. 13, 2023 Restriction Requirement dated Jan. 21, 2026.
U.S. Appl. No. 18/273,163, filed Jul. 19; 2023 Non-Final Office Action dated Feb. 3, 2026.
U.S. Appl. No. 18/274,156, filed Jul. 25, 2023 Final Office Action dated Mar. 25, 2026.
U.S. Appl. No. 18/274,436, filed Jul. 26, 2023 Final Office Action dated Mar. 25, 2026.
U.S. Appl. No. 18/289,341, filed Nov. 2, 2023 Non-Final Office Action dated Feb. 18, 2026.
U.S. Appl. No. 18/715,504, filed May 31, 2024 Non-Final Office Action dated Apr. 9, 2026.
U.S. Appl. No. 18/715,504, filed May 31, 2024 Restriction Requirement dated Feb. 4, 2026.
U.S. Appl. No. 29/939,277, filed Apr. 25, 2024 Ex Parte Quayle Action dated Feb. 23, 2026.
U.S. Appl. No. 17/552,309, filed Dec. 15, 2021 Final Office Action dated Apr. 22, 2026.
U.S. Appl. No. 17/584,101, filed Jan. 25, 2022 Non-Final Office Action dated May 14, 2026.
U.S. Appl. No. 17/689,791, filed Mar. 8, 2022 Final Office Action dated Apr. 22, 2026.
U.S. Appl. No. 17/690,908, filed Mar. 9, 2022 Final Office Action dated May 12, 2026.
U.S. Appl. No. 17/691,990, filed Mar. 10, 2022 Advisory Action dated May 27, 2026.
U.S. Appl. No. 17/709,019, filed Mar. 30, 2022 Final Office Action dated Apr. 22, 2026.
U.S. Appl. No. 17/723,210, filed Apr. 18, 2022 Final Office Action dated May 5, 2026.
U.S. Appl. No. 17/837,956, filed Jun. 10, 2022 Notice of Allowance dated May 7, 2026.
U.S. Appl. No. 17/859,995, filed Jul. 7, 2022 Final Office Action dated Apr. 28, 202.
U.S. Appl. No. 18/272,026, filed Jul. 12, 2023 Final Office Action dated Dec. 31, 2025.
U.S. Appl. No. 18/274,156, filed Jul. 25, 2023 Notice of Allowance dated Jun. 9, 2026.
U.S. Appl. No. 18/274,436, filed Jul. 26, 2023 Notice of Allowance dated Jun. 10, 2026.
U.S. Appl. No. 18/832,782, filed Jul. 24, 2024 Non-Final Office Action dated Apr. 20, 2026.
U.S. Appl. No. 18/837,098, filed Aug. 8, 2024 Non-Final Office Action dated Apr. 22, 2026.
U.S. Appl. No. 19/068,969, filed Mar. 3, 2025 Non-Final Office Action dated Apr. 28, 2026.
U.S. Appl. No. 29/939,277, filed Apr. 25, 2024 Notice of Allowance dated Jun. 10, 2026.
U.S. Appl. No. 17/690,908, filed Mar. 9, 2022 Advisory Action dated Jul. 15, 2026.
U.S. Appl. No. 17/691,990, filed Mar. 10, 2022 Non-Final Office Action dated Jun. 29, 2026.
U.S. Appl. No. 17/694,416, filed Mar. 14, 2022 Advisory Action dated Jun. 16, 2026.
U.S. Appl. No. 17/700,216, filed Mar. 21, 2022 Final Office Action dated Jun. 24, 2026.
U.S. Appl. No. 17/859,995, filed Jul. 7, 2022 Advisory Action dated Jul. 2, 2026.
U.S. Appl. No. 18/273,163, filed Jul. 19, 2023 Final Office Action dated Jul. 14, 2026.
U.S. Appl. No. 18/866,907, filed Nov. 18, 2024 Non-Final Office Action dated Jun. 29, 2026.
U.S. Appl. No. 19/018,774, filed Jan. 13, 2025 Non-Final Office Action dated Jun. 18, 2026.
U.S. Appl. No. 17/686,301, filed Mar. 3, 2022 Final Office Action dated Sep. 4, 2026.
U.S. Appl. No. 17/694,416, filed Mar. 14, 2022 Non-Final Office Action dated Aug. 19, 2026.
U.S. Appl. No. 17/859,995, filed Jul. 7, 2022 Notice of Allowance dated Sep. 1, 2026.
U.S. Appl. No. 18/272,332, filed Jul. 13, 2023 Final Office Action dated Aug. 28, 2026.
U.S. Appl. No. 18/289,341, filed Nov. 2, 2023 Final Office Action dated Aug. 18, 2026.
U.S. Appl. No. 18/715,504, filed May 31, 2024 Non-Final Office Action dated Aug. 27, 2026.
U.S. Appl. No. 19/068,969, filed Mar. 3, 2025 Final Office Action dated Sep. 1, 2026.

* cited by examiner

FIG. 1A
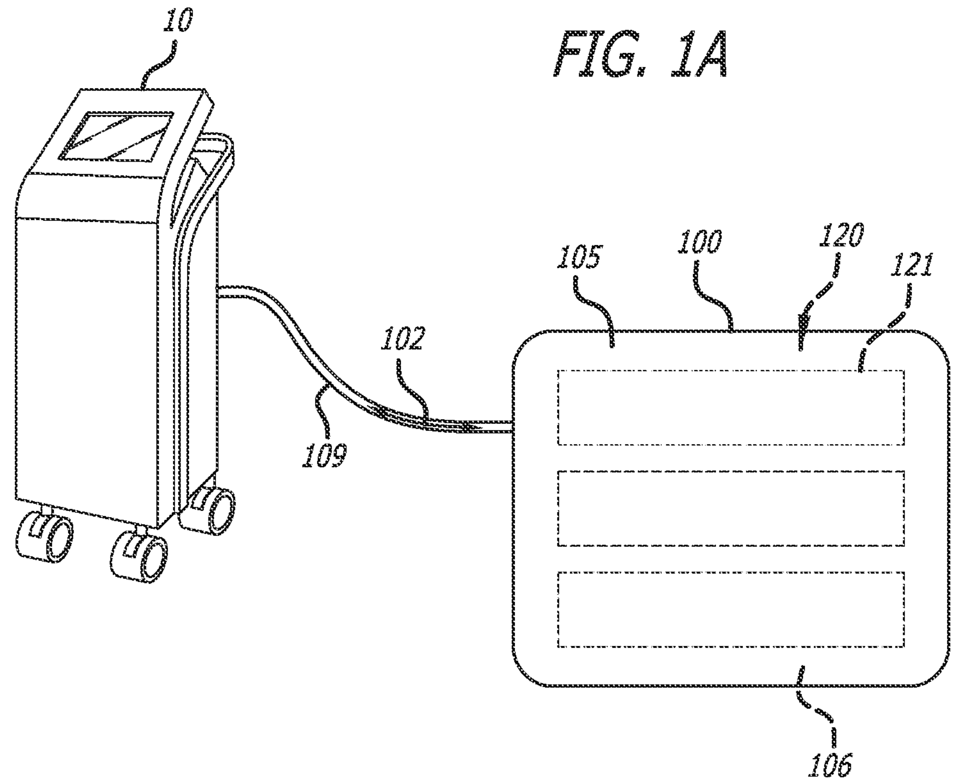
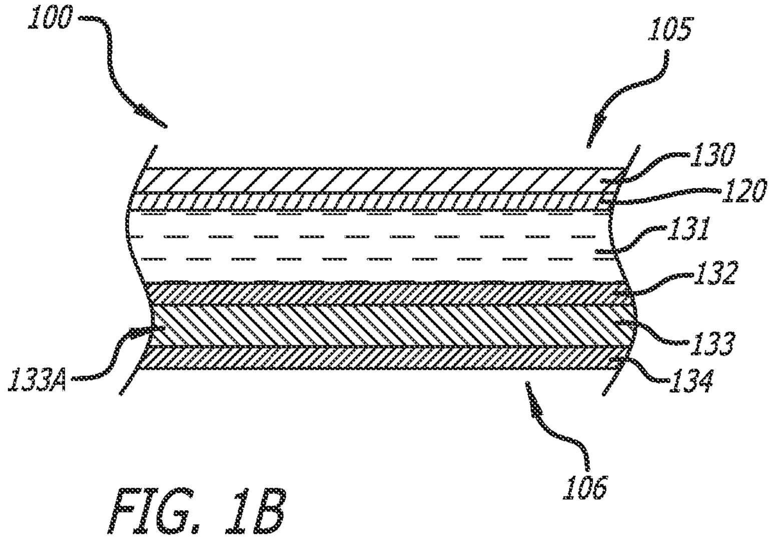
FIG. 1B

FIG. 4A
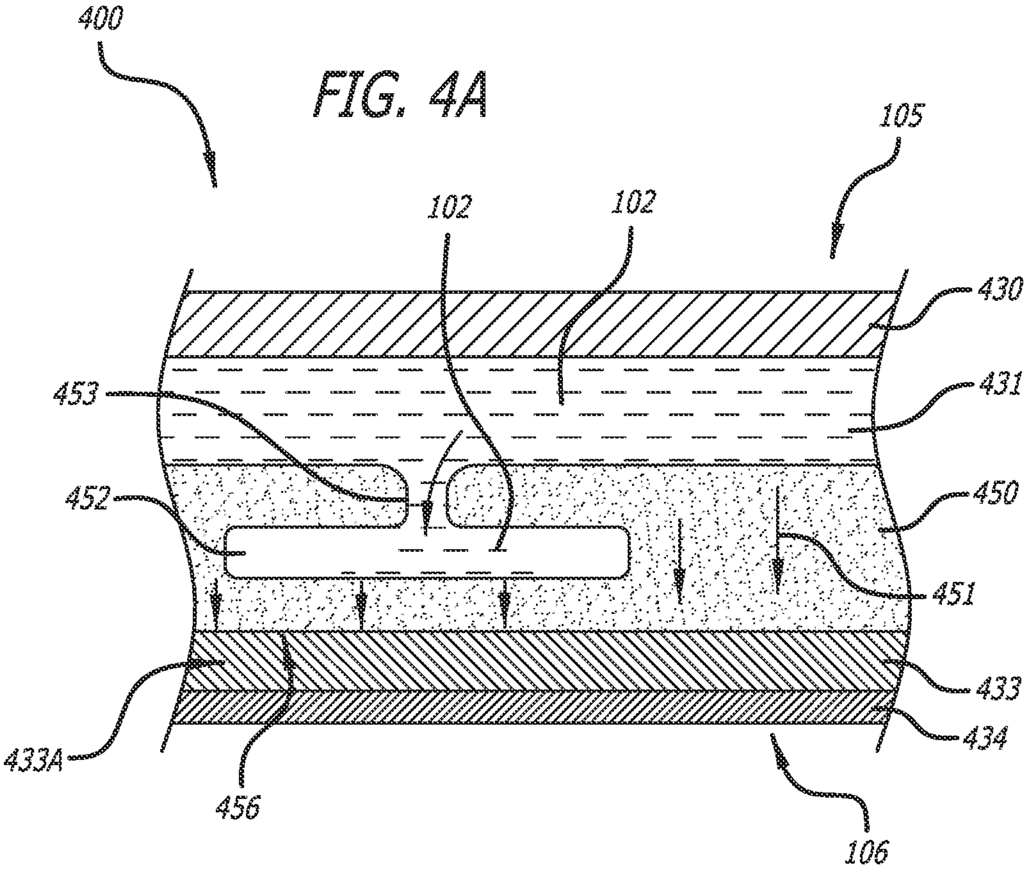
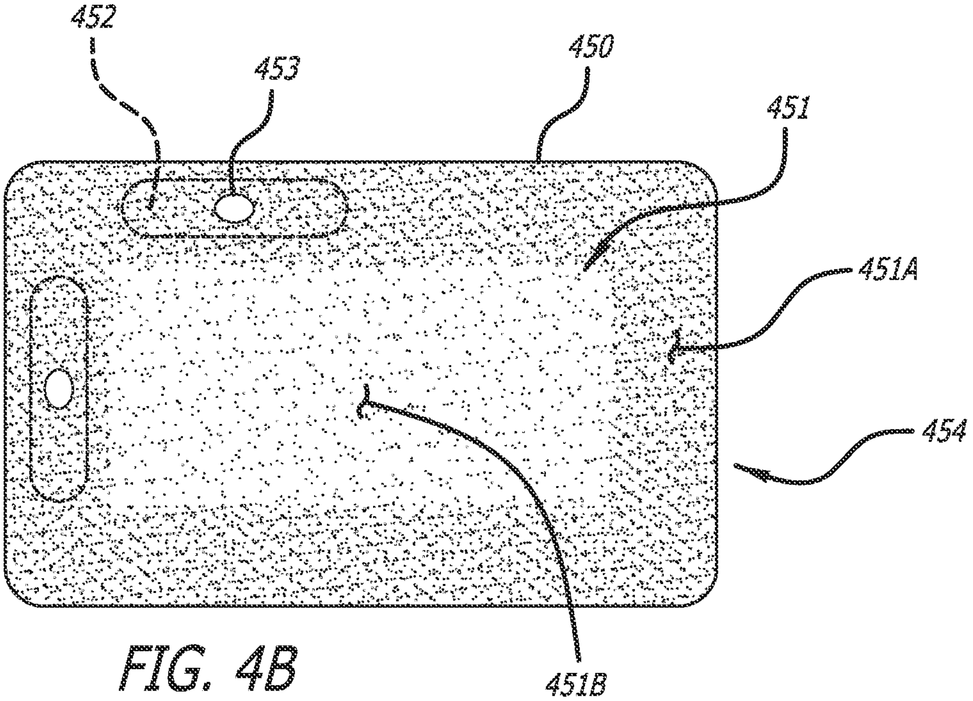
FIG. 4B

ADDED OR ALTERNATE THERMAL CONTACT PAD ADHESION

PRIORITY

This application claims the benefit of priority to U.S. Provisional Application No. 63/292,319, filed Dec. 21, 2021, which is incorporated by reference in its entirety into this application.

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g., water) through one or more thermal contact pads coupled to a patient to affect surface-to-surface thermal energy exchange with the patient. In general, TTM systems include a TTM fluid control module coupled to at least one contact pad via a fluid deliver line. One such thermal contact pad is disclosed in U.S. Pat. No. 6,197,045 titled "Cooling/heating Pad and System" filed Jan. 4, 1999, which is incorporated herein by reference in its entirety.

Applying the thermal contact pad to a non-flat surface of a patient can in some instances interrupt or inhibit thermal energy exchange with the patient due to poor thermal contact with the patient. Disclosed herein are embodiments of thermal contact pads and methods for maximizing thermal energy exchange with the patient over the contact area of the thermal contact pad.

SUMMARY OF THE INVENTION

Briefly summarized, disclosed herein is a medical pad for exchanging thermal energy between a targeted temperature management (TTM) fluid and a patient. According to some embodiments, medical pad includes a fluid containing layer configured for circulation of a TTM fluid therein, where the fluid containing layer disposed between a top side of the medical pad and a patient contact side of the medical pad. The pad further includes one or more of: (i) a bistable stiffening structure disposed along the top side of the pad; (ii) a compressible foam layer disposed between the fluid containing layer and the patient contact side; (iii) a stretchable band coupled with the fluid containing layer, the band configured to secure the pad to the patient; or (iv) a semi-permeable layer disposed along an underside of the fluid containing layer, the semi-permeable layer configured to provide for TTM fluid migration from the fluid containing layer toward the patient contact side.

In some embodiments, the pad includes the bistable stiffening structure disposed along the top side of the pad. The bistable stiffening structure is transitionable between a first stable shape and a second stable shape. The bistable stiffening structure may be disposed in the first stable shape prior to applying the pad to the patient, and transitioned away from the first stable shape after applying the pad to the patient.

In some embodiments, the bistable stiffening structure causes the pad to extend at least partially around the patient when the bistable stiffening structure is transitioned away from the first stable shape. The bistable stiffening structure may cause the pad to exert a compressive force on the patient when the bistable stiffening structure is transitioned away from the first stable shape.

In some embodiments, the pad includes the compressible foam layer and the compressible foam layer may include a thermal conductivity greater than 0.4 W/m-K, and the compressible foam layer may be disposed between the fluid containing layer and a hydrogel layer. In some embodiments, the bistable stiffening structure causes a compression of the compressible foam layer.

In some embodiments, the pad includes the stretchable band, where the stretchable band includes: a first band extension, extending away from the fluid containing layer in a first direction; and a second band extension, extending away from the fluid containing layer in a second direction opposite the first direction, and where the first band extension and/or the second band extension are configured to wrap around the patient. In some embodiments, the stretchable band is configured self-adhere to itself. In some embodiments, the stretchable band is disposed over a top-side fluid containing layer and/or disposed along an underside fluid containing layer.

In some embodiments, the pad includes the semi-permeable layer and the semi-permeable layer may be coupled with fluid containing layer so that the semi-permeable layer is in fluid communication with the fluid containing layer. In some embodiments, TTM fluid from the fluid containing layer migrates through the semi-permeable layer. In some embodiments, the pad further includes a hydrogel layer, and during use, the hydrogel layer receives TTM fluid from the semi-permeable layer.

In some embodiments, the pad defines a first permeability located along a perimeter portion of the semi-permeable layer and a second permeability located within a central portion of the semi-permeable layer, and the first permeability is greater than the second permeability.

In some embodiments, the semi-permeable layer includes one or more pockets, where each pocket is fluidly coupled with the fluid containing layer via a fluid passageway.

Also disclosed herein is a method of providing a targeted temperature management (TTM) therapy to a patient. According to some embodiments, the method includes providing a thermal contact pad that includes a fluid containing layer having a TTM fluid circulating therethrough, where the fluid containing layer is disposed between a top side of the medical pad and a patient contact side of the medical pad. The pad further includes one or more of (i) a bistable stiffening structure disposed along the top side of the pad, (ii) a compressible foam layer disposed between the fluid containing layer and the patient contact side, (iii) a stretchable band coupled with the fluid containing layer, the band configured to secure the pad to the patient, (iv) a semi-permeable layer disposed along an underside of the fluid containing layer, the semi-permeable layer configured to provide for TTM fluid migration from the fluid containing layer toward the patient contact side. The method further includes applying the pad to the patient.

In some embodiments of the method, the pad includes the bistable stiffening structure, where the bistable stiffening structure includes transition shape disposed between a first stable shape and a second stable shape, and the method further includes applying a force to the pad to transition the bistable stiffening structure away from the first stable shape across the transition shape toward the second stable shape. In some embodiments, the bistable stiffening structure causes the pad to extend at least partially around the patient when the bistable stiffening structure is transitioned toward the second stable shape, and in some embodiments, the bistable stiffening structure causes the pad to exert a compressive force on the patient when the bistable stiffening structure is transitioned toward the second stable shape.

In some embodiments of the method, the pad includes the compressible foam layer, where the compressible foam layer has a thermal conductivity greater than 0.4 W/m-K, and the compressible foam layer may be disposed between the fluid containing layer and the patient.

In some embodiments of the method, the pad includes the stretchable band, and the stretchable band includes: a first band extension, extending away from the fluid containing layer in a first direction; and a second band extension, extending away from the fluid containing layer in a second direction opposite the first direction, and the method includes wrapping the first band extension and/or the second band around the patient. In some embodiments, the stretchable band is configured self-adhere to itself.

In some embodiments of the method, the pad includes the semi-permeable layer, and a hydrogel layer, where the semi-permeable layer is fluidly coupled between the fluid containing layer and the hydrogel layer so that TTM fluid from the fluid containing layer migrates through the semi-permeable layer to the hydrogel layer. In some embodiments the semi-permeable layer defines a first permeability located along a perimeter portion of the semi-permeable layer and a second permeability located within a central portion of the semi-permeable layer, where the first permeability is greater than the second permeability. In some embodiments, the semi-permeable layer includes one or more pockets, where each pocket is fluidly coupled with the fluid containing layer via a fluid passageway.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1A illustrates a top view of first embodiment of a thermal contact pad for employment with a targeted temperature management (TTM) system, in accordance with some embodiments;

FIG. 1B is a cross-sectional side view of a portion the thermal contact pad of FIG. 1A, in accordance with some embodiments;

FIG. 4A is a cross-sectional side view of a portion of a fourth embodiment of a thermal contact pad, in accordance with some embodiments; and FIG. 4B is a top view of a semi-permeable layer of the thermal contact pad of FIG. 4A, in accordance with some embodiments.

DETAILED DESCRIPTION

Figure 1C:
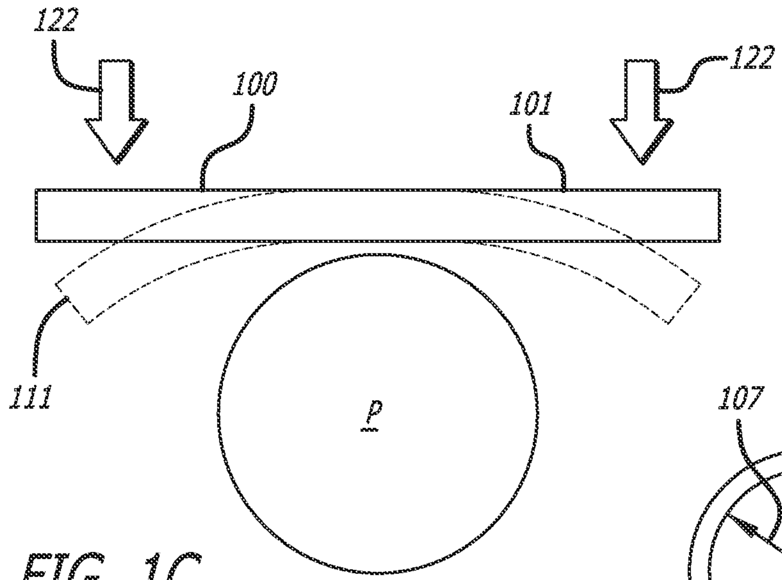
FIG. 1C is a side view of the thermal contact pad of FIG. 1A in a first stable shape, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising."

Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled to" refer to any form of interaction between two or more entities, including mechanical, fluid, and thermal interaction. Two components may be connected to or coupled with each other even though they are not in direct contact with each other. For example, two components may be coupled with each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Unless defined otherwise, all technical and scientific terms used herein have the same meaning as commonly understood by those of ordinary skill in the art.

FIGS. 1A-1E illustrate a first embodiment of a thermal contact pad 100 for employment with a targeted temperature management (TTM) system, in accordance with some embodiments. FIG. 1A is a top view of a thermal contact pad 100. The thermal contact pad (pad) 100 is configured to receive a TTM fluid 102 from a TTM module 10 via a fluid delivery line 109 and circulate the TTM fluid 102 through a fluid containing layer 131 to facilitate thermal energy exchange between the TTM fluid 102 and a patient (see FIG. 2B). The pad 100 generally defines a topside 105 configured to be disposed away from the patient P and an underside 106 configured to be disposed in contact with the patient P.

The pad 100 may generally define a rectangular shape. In other embodiments, the pad 100 may define shapes other than rectangular such as circular, oval, or a shape that matches or aligns with a shape of the human body. The pad 100 may be configured to accommodate curves of the patient body. The pad 100 includes a bistable stiffening structure 120 to define a curvature of the pad 100 in accordance with a body part such as a leg or torso, for example. The stiffening structure 120 is specifically configured to cause the pad 100 to extend around (e.g., partially around) the body part and define a contact force between the pad 100 and the body part to enhance the thermal energy exchange with the patient P.

FIG. 1B is a cross-sectional side view of a portion the pad 100, in accordance with some embodiments. The pad 100 includes multiple layers disposed between the topside 105 and the underside 106. The pad 100 generally includes a fluid containing layer 131 having TTM fluid 102 circulating therein, which defines a heat sink or a heat source for the patient P in accordance with a temperature of the TTM fluid 102. In accordance with the illustrated embodiment, the bistable stiffening structure 120 is positioned adjacent the topside 105 of the pad 100, i.e., so that the fluid containing layer 131 is disposed between the stiffening structure 120 and the underside 106.

Although not required in some embodiments, the pad 100 may include additional layers. In some embodiments, the pad 100 may include a thermal conduction layer 132, a hydrogel layer 133, and a hydrogel liner 134 which are each disposed between the fluid containing layer 131 and the underside 106. The thermal conduction layer 132 separates the TTM fluid 102 within the fluid containing layer 131 from a hydrogel 133A within the hydrogel layer 133 and facilitates thermal conduction between the TTM fluid 102 and the hydrogel 133A. The hydrogel layer 133 facilitates thermally intimate contact of the fluid containing layer 131 and the patient P. The hydrogel liner 134 is applied to the underside of the hydrogel layer 133 during manufacturing to cover the hydrogel layer 133 and encapsulate the hydrogel 133A. In use, the clinician may remove hydrogel liner 134 from the hydrogel layer 133 to expose the hydrogel 133A, thereby allowing the hydrogel 133A to contact the skin of the patient P directly. The pad 100 may also include an insulation layer 130 along the topside 105 to thermally isolate the fluid containing layer 131 from the surrounding environment. In some embodiments, the stiffening structure 120 may be disposed between the insulation layer 130 and the fluid containing layer 131. In other embodiments, the stiffening structure 120 may be positioned atop the insulation layer 130.

FIG. 1C illustrates a side view of the pad 100 disposed in an exemplary first stable shape 101, where the first stable shape is generally flat or planar. The pad 100 may be disposed in the first stable shape 101 prior to being applied to the patient P. The clinician may apply a force 122 to the pad 100 to transition the pad 100 away from the first stable shape 101 toward the second stable shape 103.

Figure 1D:
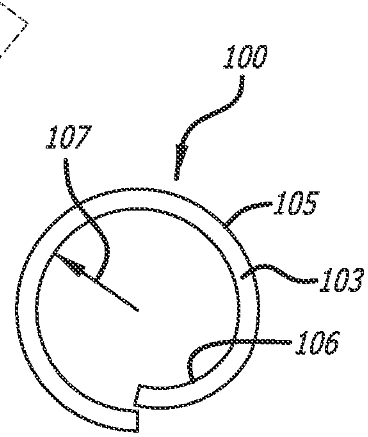
FIG. 1D is a side view of the thermal contact pad of FIG. 1A in a second stable shape, in accordance with some embodiments.

FIG. 1D illustrates a side view of the pad 100 disposed in an exemplary second stable shape 103, where the second stable shape is generally curved. In the second stable shape 103, the topside 105 is disposed on an outside of the curve and the underside 106 is disposed on an inside of the curve. In some embodiments, the second stable shape 103 may define a tubular or semi-tubular shape. The second stable shape 103 may define a radius 107 of curvature that is sufficiently small to provide for a snug fit (i.e., contact) of the pad 100 around a predetermined body part such as a leg or an arm, for example.

The bistable nature of the stiffening structure 120 provides for the pad 100 to be transitioned between the first stable shape 101 and the second stable shape 103. The stiffening structure 120 may define a transition shape 111 as shown with dotted lines in FIG. 1C. The stiffening structure 120 may be configured, such that, when the shape of the stiffening structure 120 is between the first stable shape 101 and the transition shape 111, the stiffening structure 120 self-deflects toward (i.e., springs toward) the first stable shape 101. Similarly, when the shape of the stiffening structure 120 is between the transition shape 111 and the second stable shape 103, the stiffening structure 120 self-deflects toward the second stable shape 103.

In use, the pad 100 may be disposed in the first stable shape 101 when the pad 100 is not applied to the patient and further disposed toward the second stable shape 103 when the pad 100 is applied to the patient. In some embodiments, the pad 100 may be selectively (including repeatedly) transitioned between the first stable shape 101 and the second stable shape 103.

The bistable stiffening structure 120 may include any suitable structural components to define the bistable functionality of the bistable stiffening structure 120. By way of one example, the bistable stiffening structure 120 may include one or more bistable spring strips 121 extending across the pad 100 (see FIG. 1A). The bistable spring strips

121 may function similar to a "snap bracelet" having a straight first stable shape and a curved second stable shape.

Figure 1E:
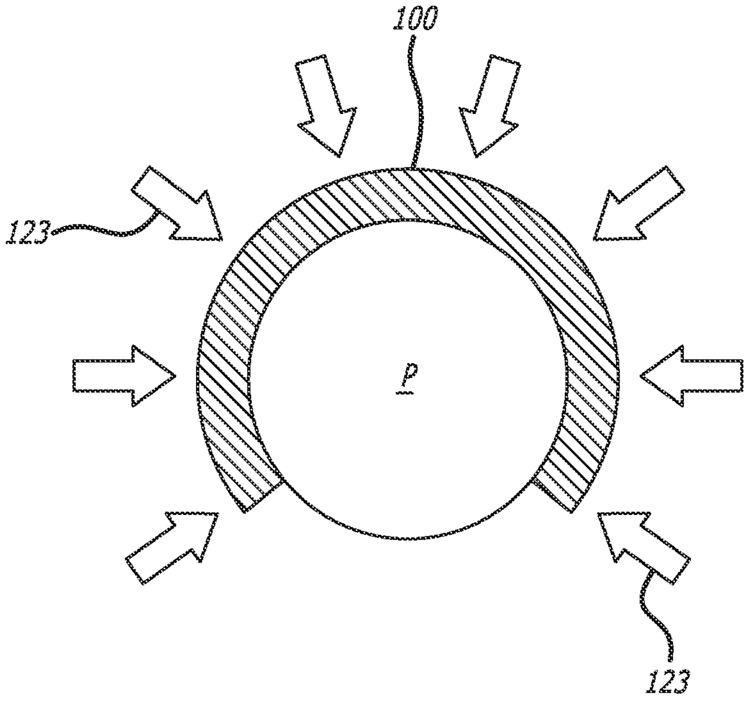
FIG. 1E illustrates a cross-sectional side view of the thermal contact pad of FIG. 1A coupled with a patient, in accordance with some embodiments.

FIG. 1E illustrates the pad 100 applied to the patient P, i.e., extending around the patient P. In some embodiments, when the pad 100 is applied to the patient P, the stiffening structure 120 may cause the pad 100 to exert a compressive force 123 on the patient P to facilitate intimate thermal contact of the pad 100 with the patient P. In further embodiments, the compressive force 123 may cause the compression of one or layers of the pad 100.

According to one method of use, the clinician may position the pad 100 adjacent the patient P at a desired location. The clinician may then transition the pad 100 from the first stable shape toward the second stable shape to cause to the pad 100 to wrap around the body part. The clinician may then initiate the thermal energy exchange process in accordance with operation of the TTM module 10. Thereafter, the clinician may urge the pad 100 toward the first stable shape to remove the pad 100 from the patient. In some embodiments, the clinician may transition the pad 100 into the first stable shape.

Figure 2A:
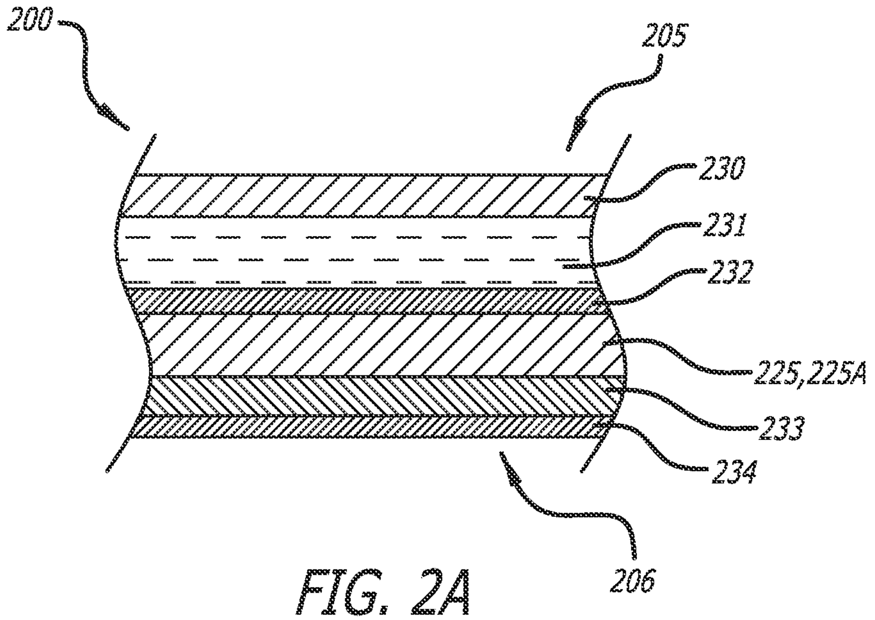
FIG. 2A is a cross-sectional side view of a portion of a second embodiment of a thermal contact pad, in accordance with some embodiments.
Figure 2B:
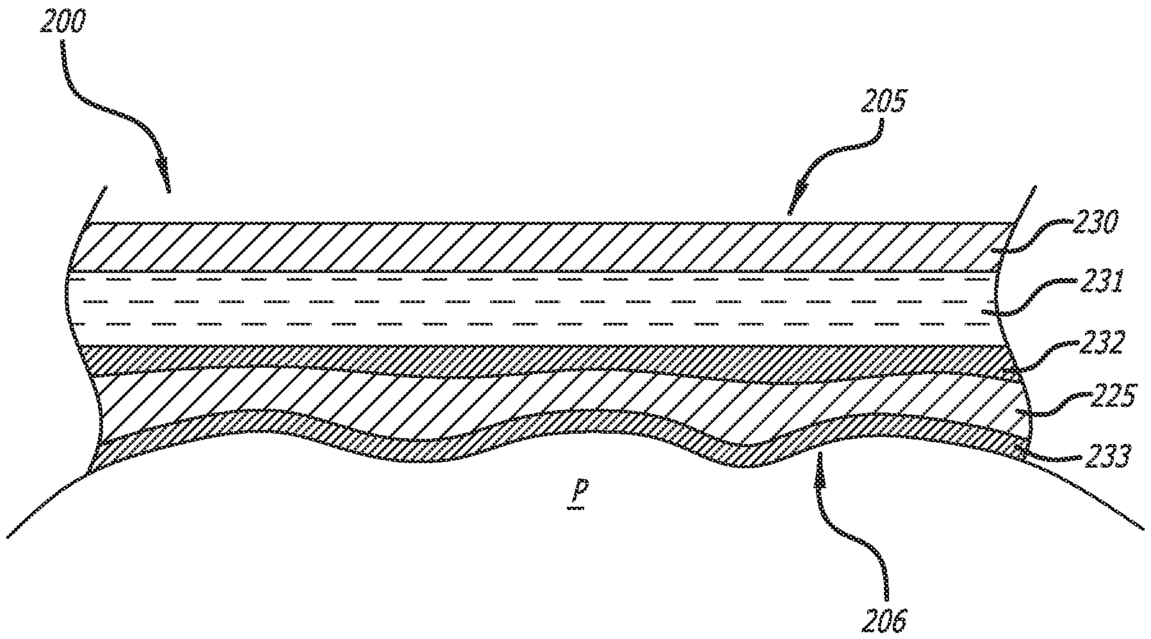
FIG. 2B illustrates a cross-sectional side view of a portion of the thermal contact pad of FIG. 2A coupled with a patient, in accordance with some embodiments.

FIGS. 2A-2B illustrate a second embodiment of a thermal contact pad 200 that can, in certain respects, resemble components of the pad 100 described in connection with FIGS. 1A-1E. It will be appreciated that all the illustrated embodiments may have analogous features. Accordingly, like features are designated with like reference numerals, with the leading digits incremented to "2." For instance, the fluid containing layer is designated as "131" in FIGS. 1A-1E, and an analogous fluid containing layer is designated as "231" in FIGS. 2A-2B. Relevant disclosure set forth above regarding similarly identified features thus may not be repeated hereafter. Moreover, specific features of the pad 100 and related components shown in FIGS. 1A-1E may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the pad of FIGS. 2A-2B. Any suitable combination of the features, and variations of the same, described with respect to the pad 100 and components illustrated in FIGS. 1A-1E can be employed with the pad and components of FIGS. 2A-2B, and vice versa. This pattern of disclosure applies equally to further embodiments depicted in subsequent figures and described hereafter.

FIG. 2A is a cross-sectional side view of a portion the pad 200, in accordance with some embodiments. The pad 200 includes a thermal foam layer 225 disposed between the fluid containing layer 231 and the hydrogel layer 233. The pad 200 may include additional layers such as are shown and described above in relation to the pad 100. The thermal foam layer 225 provides for an enhanced thermal energy exchange between the TTM fluid 102 (FIG. 1A) and the patient P (see FIG. 2B) by minimizing air gaps between the fluid containing layer 231 and the patient P.

The thermal foam layer 225 in composed of a thermally conductive foam (foam) 225A. The foam 225A is configured to conduct thermal energy (heat) between the fluid containing layer 231 and the patient P. The hydrogel layer 233 facilitates an intimate thermal contact between the thermal foam layer 225 and the patient P. In some embodiments, the foam 225A may be composed of a reticulated foam material. As discussed above, the foam 225A is configured to facilitate thermal energy exchange across the thermal foam layer 225. As such the foam 225A may be specifically configured to conduct heat and thus may include a thermal conductivity within the range of 0.4 to 0.7 W/m-K (watts per meter-Kelvin).

FIG. 2B is a cross-sectional side view of a portion the pad 200 applied to a patient P. The foam 225A is compressible (e.g., spongey) so that the thickness of the thermal foam layer 225 may vary in accordance with uneven contours of the patient P. As such, in use, the foam 225A may compress to accommodate a protrusion (i.e., a raised portion of the contour) and remain expanded to extend into a depression to eliminate an air gap that may otherwise result from a depression.

Figure 3A:
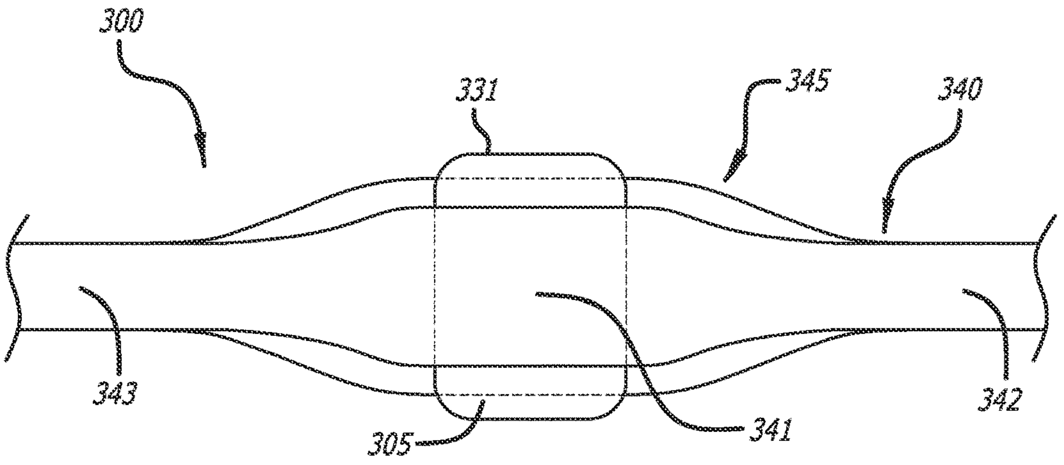
FIG. 3A is a top view of a third embodiment of a thermal contact pad, in accordance with some embodiments.
Figure 3B:
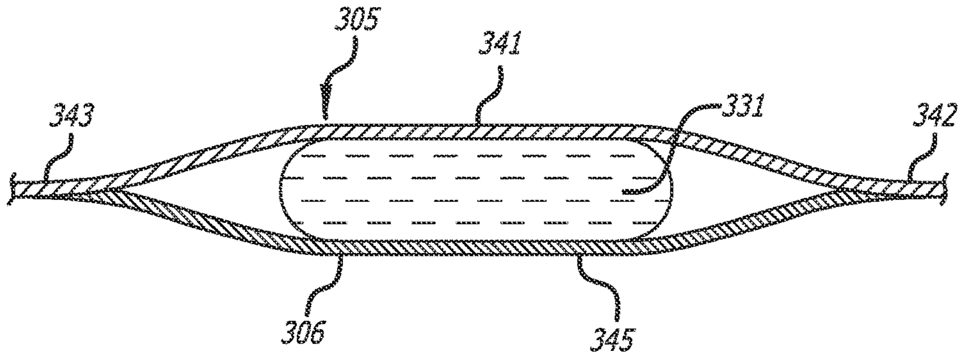
FIG. 3B illustrates a cross-sectional side view of a portion of the thermal contact pad of FIG. 3A, in accordance with some embodiments.
Figure 3C:
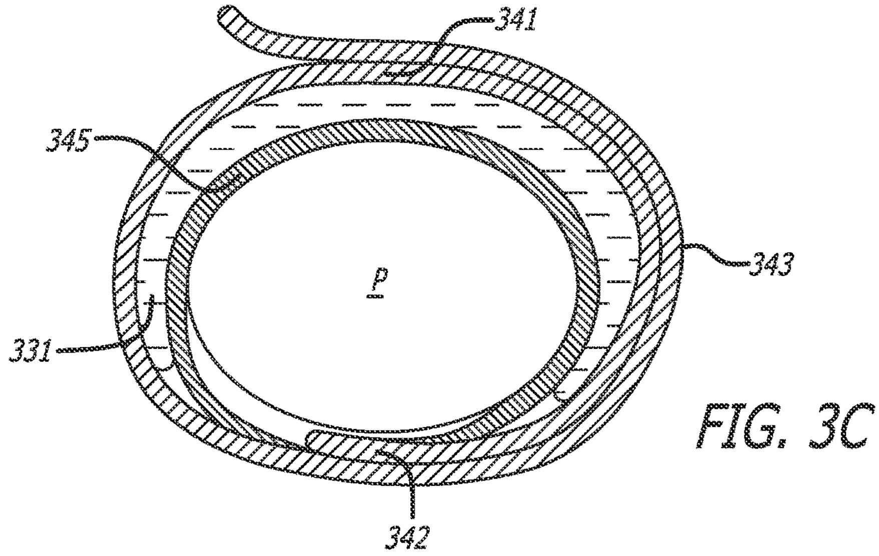
FIG. 3C illustrates a cross-sectional side view of the thermal contact pad of FIG. 3A coupled with a patient, in accordance with some embodiments.

FIGS. 3A-3C illustrate a third embodiment of a thermal contact pad 300. FIG. 3A is a top view of the pad 300 and FIG. 3B is a cross-sectional side view of a portion of the pad 300. The pad 300 generally includes a fluid containing layer 331 and a stretchable band 340 coupled with the fluid containing layer 331. The stretchable band 340 is generally configured to secure the pad 300 to the patient P. First and second band extensions 342, 343 of the stretchable band 340 extend away from the fluid containing layer 331 in opposite directions.

In the illustrated embodiment, a central portion 341 of the stretchable band 340 extends across a topside 305 of the pad 300. However, in some embodiments, the first and second band extensions 342, 343 may be coupled to opposite edges of the fluid containing layer 331 and as such, the central portion 341 of the stretchable band 340 may be omitted. In the illustrated embodiment, a bottom portion 345 of the stretchable band 340 extends across an underside 306 of the pad 300.

The band 340 is composed of a stretchable material that defines a tension when stretched. The band 340 is configured to extend around a body part in a stretched state so that the tension force secures the pad 300 to the patient. The band 340 is also composed of a self-adhering material. In other words, the band 340 (or more specifically the band material) is configured to adhere to itself without an added adhesive. The self-adhering feature of the band 340 may also facilitate an adherence of the band 340 to the patient's skin.

Although not shown, the pad 300 may include any or all of the additional layers shown and described in relation to the pad 100. In other words, in some embodiments, the pad 300 may include a thermal conduction layer, a hydrogel layer, a hydrogel liner and/or an insulation layer. For example, the pad 300 may omit the bottom portion 345 of the stretchable band 340 and include a hydrogel layer in place thereof.

FIG. 3C illustrates the pad 300 coupled with a patient P. As shown, the pad 300 may extend around the patient P, such as partially around a portion of the patient P. The band 340 extends around the patient P to secure the pad 300 to the patient P. In some embodiments, the band 340 is wrapped over itself and secured to itself. The bottom portion 345 of the band 340 is disposed between the fluid containing layer 331 and the patient P. The first band extension 342 is coupled with the patient P, i.e., the band extension 342 extends along the skin and is in contact with skin. The second band extension 343 extends over the top of the first band extension 341 and may, in some instances, extend over the top of the central portion 341. In some instances, the second band extension 343 may wrap over the first band extension 341 (including the fluid containing layer 331) multiple times.

In use, the clinician may position the pad on the patient at a desired location. Thereafter, the clinician may stretch the band to establish a tension in the band and wrap one or both band extension around the patient.

FIGS. 4A-4B illustrate a fourth embodiment of a thermal contact pad 400. In some instances, the hydrogel of a hydrogel layer of a thermal contact pad may dry out during use resulting in over-adhesion of the hydrogel with the skin of the patient and may also result in a decrease in thermal energy exchange through the hydrogel. The thermal contact pad 400 is configured to inhibit the drying-out tendency of the hydrogel over the course of a TTM therapy.

FIG. 4A is a cross-sectional side view of a portion of the pad 400. As shown, the pad 400 generally includes a fluid containing layer 431 and a semi-permeable layer 450 disposed between the fluid containing layer 431 and a hydrogel layer 433. The semi-permeable layer 450 is configured to allow water from the fluid containing layer 431 to migrate toward the hydrogel layer 433 thereby inhibiting the hydrogel 433A from drying out.

The semi-permeable layer 450 is composed of a material (e.g., a foam material) that is semi-permeable to water. In other words, semi-permeable layer 450 provides for a migration of water from the fluid containing layer 431 to the hydrogel layer 433 at a rate that maintains an appropriate concentration of water within the hydrogel 433A.

In some embodiments, although not required, the semi-permeable layer 450 may include one or more pockets 452 that are fluidly coupled with the fluid containing layer 431 via a fluid passageway 453. The pockets 452 may contain a volume of TTM fluid 102 (water) from the fluid containing layer 431 to facilitate the migration of water through the semi-permeable layer 450. The number and location of the pockets 452 may define a desired permeability 451 across the semi-permeable layer 450 as further described below. In some embodiments, the permeability 451 may be defined by the material of the semi-permeable layer 450. In other embodiments, the semi-permeable layer 450 may include a semi-permeable membrane (not shown) disposed across the semi-permeable layer 450, such as adjacent a bottom side 456 of the semi-permeable layer 450, for example.

FIG. 4B illustrates a top view of the semi-permeable layer 450. Shown are the one or more pockets 452 including the fluid passageway 453. Also illustrated is a variation in the permeability 451 illustrated as a varying dot density. In some instances, the hydrogel 433A may dry out at locations along the perimeter edge of the hydrogel layer 433 at a greater rate than at locations toward the center of the hydrogel layer 433. As such, a permeability 451A along perimeter regions of the semi-permeable layer 450 may be greater than a permeability 451B at central regions of the semi-permeable layer 450. In a similar fashion, a number or density of the pockets 452 may be greater along the along perimeter regions than within the central region. In some embodiments, the semi-permeable layer 450 may include a non-permeable border 454 to prevent water from seeping out of the semi-permeable layer 450 along the perimeter edge.

As discussed above, each of the illustrated embodiments of pads 100-400 includes one or more features that are not included in the illustrated embodiments of the other pads. However, other embodiments of the pads 100-400 may include any or all features of the other pads or any combination of the features described in relation to the pads 100-400.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A medical pad for exchanging thermal energy with a patient, the pad comprising:
- a length extending at least partially around the patient, the length extending between a first perimeter edge of the pad and a second perimeter edge opposite the first perimeter edge of the pad;
- a bistable stiffening structure disposed along a top side of the pad, the bistable stiffening structure extending away from the first perimeter edge across a midpoint of the pad toward the second perimeter edge;
- a fluid containing layer configured for circulation of a TTM fluid therein, the fluid containing layer disposed on a bottom side of the bistable stiffening structure;
- a thermal conduction layer disposed on a bottom side of the fluid containing layer; and
- a hydrogel layer containing hydrogel disposed along a bottom side of the thermal conduction layer,
- wherein the thermal conduction layer separates the TTM fluid from the hydrogel.

2. The medical pad according to claim 1, wherein the bistable stiffening structure is transitionable between a first stable shape and a second stable shape.

3. The medical pad according to claim 2, wherein the first stable shape is a planar shape and the second stable shape is a curved shape.

4. The medical pad according to claim 2, wherein:
- the bistable stiffening structure is disposed in the first stable shape prior to applying the pad to the patient, and
- the bistable stiffening structure is transitioned away from the first stable shape after applying the pad to the patient.

5. The medical pad according to claim 4, wherein:
- the bistable stiffening structure maintains the bistable stiffening structure in the first stable shape prior to applying the pad to the patient, and
- the bistable stiffening structure urges the bistable stiffening structure toward the second stable shape after applying the pad to the patient.

6. The medical pad according to claim 2, wherein the bistable stiffening structure causes the pad to extend at least partially around the patient when the bistable stiffening structure is transitioned away from the first stable shape.

7. The medical pad according to claim 2, wherein the bistable stiffening structure causes the pad to exert a compressive force on the patient when the bistable stiffening structure is transitioned away from the first stable shape.

8. The medical pad according to claim 7, wherein the bistable stiffening structure causes the pad to exert a compressive force on the patient along an entire length of the pad.

9. The medical pad according to claim 1, further comprising a compressible foam layer.

10. The medical pad according to claim 9, wherein the compressible foam layer includes a thermal conductivity greater than 0.4 W/m-K.

11. The medical pad according to claim 9, wherein the compressible foam layer is disposed between the fluid containing layer and the hydrogel layer.

12. The medical pad according to claim 9, wherein in use, the bistable stiffening structure causes a compression of the compressible foam layer.

13. The medical pad according to claim 1, further comprising a stretchable band.

14. The medical pad according to claim 13, wherein the stretchable band includes:

a first band extension extending away from the fluid containing layer in a first direction; and a second band extension extending away from the fluid containing layer in a second direction opposite the first direction, wherein the first band extension and/or the second band extension are configured to wrap around the patient.

15. The medical pad according to claim 13, wherein the stretchable band is configured self-adhere to itself.

16. The medical pad according to claim 13, wherein a central portion of the stretchable band is disposed over a topside of the fluid containing layer.

17. The medical pad according to claim 13, wherein a bottom portion stretchable band is disposed along an underside fluid containing layer.

18. The medical pad according to claim 1, further comprising a semi-permeable layer.

19. The medical pad according to claim 18, wherein the semi-permeable layer is coupled with the fluid containing layer so that the semi-permeable layer is in fluid communication with the fluid containing layer.

20. The medical pad according to claim 19, wherein during use, TTM fluid from the fluid containing layer migrates through the semi-permeable layer.

21. The medical pad according to claim 20, further comprising the hydrogel layer, wherein during use, the hydrogel layer receives TTM fluid from the semi-permeable layer.

22. The medical pad according to claim 18, wherein:

the semi-permeable layer defines:

a first permeability located along a perimeter portion of the semi-permeable layer, and a second permeability located within a central portion of the semi-permeable layer, and the first permeability is greater than the second permeability.

23. The medical pad according to claim 18, wherein:

the semi-permeable layer includes one or more pockets, and each pocket is fluidly coupled with the fluid containing layer via a fluid passageway.

* * * * *